US010080894B2

(12) United States Patent
Richter et al.

(10) Patent No.: US 10,080,894 B2
(45) Date of Patent: Sep. 25, 2018

(54) SYSTEMS AND METHODS FOR NEUROMODULATION DEVICE CODING WITH TRANS-SPECIES LIBRARIES

(71) Applicants: NORTHWESTERN UNIVERSITY, Evanston, IL (US); Resonance Medical, LLC, Evanston, IL (US)

(72) Inventors: Claus-Peter Richter, Skokie, IL (US); Chris Heddon, Evanston, IL (US); Petrina LaFaire, Chicago, IL (US); Brian Dougherty, Mequon, WI (US)

(73) Assignees: NORTHWESTERN UNIVERSITY, Evanston, IL (US); RESONANCE MEDICAL, LLC, Evanston, IL (US)

( * ) Notice: Subject to any disclaimer, the term of this patent is extended or adjusted under 35 U.S.C. 154(b) by 82 days.

(21) Appl. No.: 14/743,478

(22) Filed: Jun. 18, 2015

(65) Prior Publication Data
US 2015/0367131 A1    Dec. 24, 2015

Related U.S. Application Data

(60) Provisional application No. 62/013,853, filed on Jun. 18, 2014.

(51) Int. Cl.
*A61N 1/36* (2006.01)
*A61N 1/05* (2006.01)

(52) U.S. Cl.
CPC ....... *A61N 1/36032* (2013.01); *A61N 1/0541* (2013.01); *A61N 1/36036* (2017.08)

(58) Field of Classification Search
CPC ........ A61N 1/36; A61N 1/05; A61N 1/36032; A61N 1/0541
(Continued)

(56) References Cited

U.S. PATENT DOCUMENTS 5,729,694 A * 3/1998 Holzrichter ............. G10L 15/24
 704/270
6,289,247 B1 * 9/2001 Faltys ................ A61N 1/36036
 607/55
(Continued)

FOREIGN PATENT DOCUMENTS

WO    2014113891 A1    7/2014

OTHER PUBLICATIONS

Swaminathan et al., "Psychophysiological Analyses Demonstrate the Importance of Neural Envelope Coding for Speech Perception in Noise", The Journal of Neuroscience, Feb. 1, 2012.
(Continued)

*Primary Examiner* — Amanda Hulbert
*Assistant Examiner* — Roland Dinga
(74) *Attorney, Agent, or Firm* — Locke Lord LLP; Tim Tingkang Xia, Esq.

(57) ABSTRACT

Aspects of the invention include systems and methods for neuromodulation device coding with a neural code library. The method includes identifying a pattern of a sensory signal, retrieving one or more digital representations of a neural response corresponding to the identified pattern from a neural code library, where the neural code library comprises a plurality of digital representations of neural responses of neural units corresponding to each pattern, selecting one or more neural units of a patient to be stimulated by a neuromodulation device associated with the patient based on the retrieved one or more digital representations of a neural response pattern, and stimulating the selected neural units of the patient.

47 Claims, 10 Drawing Sheets
(9 of 10 Drawing Sheet(s) Filed in Color)

(58) Field of Classification Search
USPC .................................. 607/55, 57, 137, 116
See application file for complete search history.

(56) References Cited

U.S. PATENT DOCUMENTS

| | | | |
|---|---|---|---|
| 7,941,223 B2 | 5/2011 | Zierhofer et al. | |
| 8,265,286 B2 | 9/2012 | Segel et al. | |
| 2005/0177205 A1* | 8/2005 | Kwon | A61N 1/36032 607/57 |
| 2011/0004273 A1* | 1/2011 | Van den Heuvel | A61N 1/36032 607/57 |
| 2012/0310140 A1 | 12/2012 | Kramer et al. | |

OTHER PUBLICATIONS

International Search Report and Written Opinion for PCT/US2015/036490 dated Sep. 21, 2015, ISA/US.
Clark, G. 1995. Cochlear implants: it's time to rethink. Am J Otol 16, 120-1; author reply 122-3.
Clark, G. 2003. Cochlear Implants: Fundamentals and Applications Springer, New York.
Dallos, P. 1973. The auditory periphery: Biophysics and physiology. In: Dallos, P., (Ed.), The auditory periphery: Biophysics and physiology. Academic Press, New York.
Dallos, P. 1992. The active cochlea. J Neurosci 12, 4575-85.
Dallos, P. 2003. Organ of Corti kinematics. J Assoc Res Otolaryngol 4, 416-21.
Davis, H. 1983. An active process in cochlear mechanics. Hear Res 9, 79-90.
Davis, R.O. 1986. The Personal Acoustics Lab (PAL): a microcomputer-based system for digital signal acquisition, analysis, and synthesis. Comput Methods Programs Biomed 23, 199-210.
Dudley, H. 1939. The Automatic Synthesis of Speech. Proceedings of the National Academy of Sciences of the United States of America 25, 377-83.
Durand, L.G., Pibarot, P. 1995. Digital signal processing of the phonocardiogram: review of the most recent advancements. Crit Rev Biomed Eng 23, 163-219.
Edgerton, B.J., Brimacombe, J.A. 1984. Effects of signal processing by the House-3M cochlear implant on consonant perception. Acta Otolaryngol Suppl 411, 115-23.
Edwards, E., Chang, E.F. 2013. Syllabic (approximately 2-5 Hz) and fluctuation ( approximately 1-10 Hz) ranges in speech and auditory processing. Hearing research 305, 113-34.
Erickson, M.L., D'Alfonso, A.E. 2002. A comparison of two methods of formant frequency estimation for high-pitched voices. J Voice 16, 147-71.
Fishman, K.E., Shannon, R. V., and Slattery, W. H. 1997. Speech recognition as a function of the number of electrodes used in the SPEAK cochlear implant speech processor. Journal of Speech, Language and Hearing Research, 1201-1215.
Flint, P.W., Haughey, B. H., Lund, V. J., Niparko, J. K., Richardson, M. A., Robbins, K. T., & Thomas, J. R. 2010. Cummings Otolaryngology—Head and Neck Surgery Mosby Elsevier, Philadelphia Pa.
Garnham, C., O'Driscoll, M., Ramsden, Saeed, S. 2002. Speech understanding in noise with a Med-El COMBI 40+ cochlear implant using reduced channel sets. Ear and hearing 23, 540-52.
Gaubitch, N.D., Ward, D.B., Naylor, P.A. 2006. Statistical analysis of the autoregressive modeling of reverberant speech. The Journal of the Acoustical Society of America 120, 4031-9.
Hochmair, E.S., Hochmair-Desoyer, I.J., Burian, K. 1979. Experience with implanted auditory nerve stimulator. Trans Am Soc Artif Intern Organs 25, 357-61.
Hudspeth, A.J. Oct. 5, 1989. How the ear's works work. Nature 341, 397-404.
Kiefer, J., von Ilberg, C., Rupprecht, V., Hubner-Egner, J., Knecht, R. 2000. Optimized speech understanding with the continuous interleaved sampling speech coding strategy in patients with cochlear implants: effect of variations in stimulation rate and number of channels. The Annals of otology, rhinology, and laryngology 109, 1009-20.
Kob, M., Neuschaefer-Rube, C. 2002. A method for measurement of the vocal tract impedance at the mouth. Med Eng Phys 24, 467-71.
Prather, J.F. 2013. Auditory signal processing in communication: perception and performance of vocal sounds. Hearing research 305, 144-55.
Rubinstein, J.T. 2004. How cochlear implants encode speech. Current opinion in otolaryngology and head and neck surgery 12, 444-448.
Scott, S.K., McGettigan, C. 2013. The neural processing of masked speech. Hearing research 303, 58-66.
Somek, B., Fajt S., Dembitz, A., Ivkovic, M., & Ostojic, J. 2006. Coding Strategies for Cochlear Implants AUTOMATIKA: casopis za automatiku, mjerenje, elektroniku, racunarstvo I komunikasije 47.
Stephens, J.D., Holt, L.L. 2011. A standard set of American-English voiced stop-consonant stimuli from morphed natural speech. Speech Commun 53, 877-888.
von Békésy, G. 1960. Experiments in Hearing McGraw-Hill Book Company, New York.
Wang, S., Mannell, R., Newall, P., Han, D. 2011. Contribution of spectral cues to mandarin lexical tone recognition in normal-hearing and hearing-impaired Mandarin Chinese speakers. Ear Hear 32, 97-103.
Wang, X. 2013. The harmonic organization of auditory cortex. Front Syst Neurosci 7, 114. Wilson, B.S. 1997. The future of cochlear implants. British journal of audiology 31, 205-25.
Wilson, B.S., Dorman, M.F. 2008. Cochlear implants: a remarkable past and a brilliant future. Hearing research 242, 3-21.
French NR, Steinberg JC. 1947. Factors governing the intelligibility of speech sounds. JASA 19, 90-119.
Clark, G. M., Dowell, R. C., Pyman, B. C., Brown, A. M., Webb, R. L., Tong, Y. C., . . . Seligman, P. M. (1984). Clinical trial of a multi-channel cochlear prosthesis: results on 10 postlingually deaf patients. Aust N Z J Surg, 54(6), 519-526.
Clark, G. M., Tong, Y. C., Patrick, J. F., Seligman, P. M., Crosby, P. A., Kuzma, J. A., and Money, D. K. (1984). A multi-channel hearing prosthesis for profound-to-total hearing loss. J Med Eng Technol, 8(1), 3-8.
Djourno, A., and Eyries, C. (1957). [Auditory prosthesis by means of a distant electrical stimulation of the sensory nerve with the use of an indwelt coiling]. Presse Med, 65(63), 1417.
Doyle, J. B., Jr., Doyle, J. H., Turnbull, F. M., Abbey, J., and House, L. (1963). Electrical Stimulation in Eighth Nerve Deafness. A Preliminary Report. Bull Los Angel Neuro Soc, 28, 148-150.
House, W. F., and Berliner, K. I. (1982). The cochlear implant. Otolaryngol Clin North Am, 15(4), 917-923.
House, W. F., and Edgerton, B. J. (1982). A multiple-electrode cochlear implant. Ann Otol Rhinol Laryngol Suppl, 91(2 Pt 3), 104-116.
Lawson, D. T., Wilson, B. S., & Finley, C. C. (1993). New processing strategies for multichannel cochlear prostheses. Prog Brain Res, 97, 313-321.
Shannon, R. V. (1981). Growth of loudness for sinusoidal and pulsatile electrical stimulation. Ann Otol Rhinol Laryngol Suppl, 90(2 Pt 3), 13-14.
Shannon, R. V. (1983). Multichannel electrical stimulation of the auditory nerve in man. II. Channel interaction. Hear Res, 12(1), 1-16.
Shannon, R. V. (1985). Threshold and loudness functions for pulsatile stimulation of cochlear implants. Hear Res, 18(2), 135-143.
Shannon, R. V., Fu, Q. J., and Galvin, J., 3rd. (2004). The number of spectral channels required for speech recognition depends on the difficulty of the listening situation. Acta Otolaryngol Suppl(552), 50-54.
Simmons, F. B., Dent, L. J., and Van Compernolle, D. (1986). Comparison of different speech processing strategies on patients receiving the same implant. Ann Otol Rhinol Laryngol, 95(1 Pt 1), 71-75.

(56) References Cited

OTHER PUBLICATIONS

Wilson, B. S. (1997). The future of cochlear implants. Br J Audiol, 31(4), 205-225.

Wilson, B. S., Finley, C. C., Lawson, D. T., Wolford, R. D., Eddington, D. K., and Rabinowitz, W. M. (1991). Better speech recognition with cochlear implants. Nature, 352(6332), 236-238.

Wilson, B. S., Finley, C. C., Lawson, D. T., Wolford, R. D., and Zerbi, M. (1993). Design and evaluation of a continuous interleaved sampling (CIS) processing strategy for multichannel cochlear implants. J Rehabil Res Dev, 30(1), 110-116.

* cited by examiner

| N | word | | | | | | | |
|---|---|---|---|---|---|---|---|---|
| | word played | word selected | | | | | | |
| 1 | bomb | wood | 3 | dime | 0 | bomb | 5 | goose | 0 |
| 2 | shore | shore | 1 | hate | 2 | van | 4 | knife | 1 |
| 3 | bean | cape | 1 | bean | 0 | tooth | 2 | make | 1 |
| 4 | merge | seize | 1 | mess | 2 | jar | 3 | merge | 2 |
| 5 | ditch | shore | 0 | ditch | 6 | tough | 2 | king | 0 |
| 6 | sun | sun | 4 | knife | 1 | lag | 3 | shore | 0 |
| 7 | tough | goose | 3 | tough | 4 | tooth | 1 | jug | 0 |
| 8 | seize | gale | 5 | seize | 0 | thin | 3 | merge | 0 |
| 9 | lease | patch | 3 | ripe | 3 | make | 2 | lease | 0 |
| 10 | home | yearn | 0 | home | 3 | toad | 3 | check | 2 |
| 11 | jar | jar | 2 | june | 2 | gale | 0 | toad | 4 |
| 12 | fall | dead | 8 | toad | 0 | fall | 0 | loop | 0 |
| 13 | van | van | 2 | lease | 2 | ditch | 3 | toad | 1 |
| 14 | make | rose | 1 | patch | 3 | make | 3 | yearn | 1 |
| 15 | tooth | kite | 4 | wish | 4 | tooth | 0 | seize | 0 |
| 16 | patch | patch | 5 | yearn | 0 | check | 1 | tough | 2 |
| 17 | hate | merge | 0 | hate | 3 | fit | 5 | king | 0 |
| 18 | knife | wish | 2 | make | 3 | van | 2 | knife | 1 |
| 19 | boat | name | 1 | wish | 0 | boat | 6 | mess | 1 |
| 20 | dead | dead | 2 | chore | 1 | patch | 5 | knife | 0 |
| 21 | goose | wreck | 6 | goose | 0 | salve | 0 | patch | 2 |

FIG. 8

|  | run1 | | run2 | | | |
| --- | --- | --- | --- | --- | --- | --- |
|  | correct | wrong | correct | correct twice | wrong | wrong twice |
|  | 3 | 3 | 3 | 2 | 4 | 2 |
|  | 2 | 3 | 0 | 0 | 4 | 2 |
|  | 0 | 4 | 0 | 0 | 3 | 1 |
|  | 0 | 5 | 2 | 0 | 3 | 0 |
|  | 4 | 2 | 2 | 2 | 3 | 0 |
|  | 1 | 4 | 0 | 0 | 4 | 0 |
|  | 2 | 2 | 2 | 2 | 2 | 1 |
|  | 0 | 4 | 0 | 0 | 4 | 4 |
|  | 1 | 5 | 0 | 0 | 4 | 3 |
|  | 4 | 2 | 1 | 1 | 4 | 1 |
|  | 3 | 3 | 2 | 0 | 5 | 2 |
|  | 1 | 5 | 2 | 1 | 4 | 4 |
|  | 1 | 4 | 0 | 0 | 4 | 4 |
|  | 0 | 4 | 4 | 0 | 1 | 0 |
|  | 0 | 6 | 1 | 0 | 5 | 4 |
|  | 3 | 2 | 2 | 2 | 2 | 0 |
|  | 2 | 3 | 1 | 1 | 3 | 2 |
|  | 0 | 4 | 1 | 0 | 3 | 2 |
|  | 5 | 1 | 4 | 4 | 1 | 0 |
|  | 2 | 2 | 2 | 2 | 2 | 1 |
|  | 0 | 4 | 0 | 0 | 4 | 4 |
| total count | 34 | 72 | 29 | 17 | 69 | 37 |
| percent | 32.08 | 67.92 | 29.59 | 17.35 | 70.41 | 37.76 |
| recognized (%) |  |  |  |  |  | 55.1 |

FIG. 9

SYSTEMS AND METHODS FOR NEUROMODULATION DEVICE CODING WITH TRANS-SPECIES LIBRARIES

CROSS-REFERENCE TO RELATED PATENT APPLICATION

This application claims the benefit, pursuant to 35 U.S.C. § 119(e), of U.S. provisional patent application Ser. No. 62/013,853, filed Jun. 18, 2014, entitled "COCHLEAR IMPLANT CODING WITH TRANS-SPECIES LIBRARIES," by Chris Heddon et al., which is incorporated herein by reference in its entirety.

Some references, which may include patents, patent applications and various publications, are cited in a reference list and discussed in the description of this invention. The citation and/or discussion of such references is provided merely to clarify the description of the invention and is not an admission that any such reference is "prior art" to the invention described herein. All references cited and discussed in this specification are incorporated herein by reference in their entireties and to the same extent as if each reference was individually incorporated by reference.

STATEMENT AS TO RIGHTS UNDER FEDERALLY-SPONSORED RESEARCH

This invention was made with government support under R01 DC011855 awarded by the National Institutes of Health. The government has certain rights in the invention.

FIELD OF THE INVENTION

The invention relates generally to the neural stimulation, particularly to systems and methods for neuromodulation device coding with trans-species libraries, and more particularly to systems and methods for cochlear implant coding with trans-species neural code libraries.

BACKGROUND OF THE INVENTION

The background description provided herein is for the purpose of generally presenting the context of the invention. The subject matter discussed in the background of the invention section should not be assumed to be prior art merely as a result of its mention in the background of the invention section. Similarly, a problem mentioned in the background of the invention section or associated with the subject matter of the background of the invention section should not be assumed to have been previously recognized in the prior art. The subject matter in the background of the invention section merely represents different approaches, which in and of themselves may also be inventions. Work of the presently named inventors, to the extent it is described in the background of the invention section, as well as aspects of the description that may not otherwise qualify as prior art at the time of filing, are neither expressly nor impliedly admitted as prior art against the invention.

Cochlear implants are considered the most successful neural prostheses. They restore some hearing for more than 320,000 severe-to-profound deaf individuals by stimulating segments along the length of the tonotopically organized cochlear spiral ganglion. The devices include three essential components, the speech processor, the transcutaneous transmitter and receiver, and the cochlear implant array. The devices record and process sound signals and convert acoustic information of the sound signals into electric pulse trains that are used to directly stimulate the auditory nerve. Over the last two decades, the improvement of the coding strategies for acoustic information was the main contributor to the improvement of the cochlear implants. Still, room exists to advance the technology.

Communication describes the transfer of information between individuals, such as speech. Acoustic information is processed at a rapid speed by the brain, at about three to seven syllables per second (Edwards and Chang, 2013; Prather, 2013; Scott and McGettigan, 2013; Wang, 2013). Vocal cords are set in vibration by airflow. The vibrations are modulated by the actions of the larynx, pharynx, lips, teeth, tong, and the upper airway. Changes in frequency and intensity are used to code information in an acoustic signal. The listener uses the resulting acoustic patterns, or acoustic cues, to decode the information. Complex signal processing by the brain allows speech perception under challenging listening conditions. At the other end of the transmission line, the ear decodes the acoustic signal (Clark, 1995; Clark, 2003). The inner ear acts as a frequency analyzer and converts acoustically induced vibrations of the inner ear soft tissue structures into series of action on the auditory nerve (von Békésy, 1960; Dallos, 1973; Davis, 1983; Hudspeth, 1989 Oct 5; Dallos, 1992; Dallos, 2003). The brain can use the information provided for communication. As indicated, acoustic information comprises of complex acoustic patterns that are constantly changing. According to the articulation different classes can be distinguished, vowels, semivowels, diphthongs, nasal consonants, stops, fricatives and affricatives. Several theories have been developed of how the information is processed, including the active theories such as the "*Motor Theory*" by Liberman, and the "*Analysis-by-Synthesis Theory*" by Stevens and Halle and the passive theories that emphasize speech perception the passive filtering of the acoustic signal by the listener. Moreover the "*Quantal Theory*", and the "*Action Theory*" have been proposed.

Vocoders are systems that analyze, transmit and synthesize speech. They provided the basis for the development of cochlear implant speech processors. One of the early systems was presented by Dudley (Dudley, 1939). The system includes a set of bandpass filters, and the amplitude in each of the filters was measured continuously, as was the fundamental frequency of the speech. The responses from the bandpass filters were used to control the output of the system. About 2 to 4 filter bands were required for intelligible speech in quiet listening environments (Shannon, Fu, and Galvin, 2004). However, for more challenging listening conditions or for music perception more independent channels are required to code the acoustic information; 16 and more for speech in noise and 30 and more for music perception (Shannon et al., 2004). The number of electrode contacts in contemporary cochlear implants is related to the number of critical bands for optimal speech transmission, about 14 to 19 critical bands over the speech frequency range.

In initial attempts to encode the acoustic information, a single stimulation electrode was used (for a review see Clark, 2003). While this simple coding strategy provided the patients with information about syllables, words, phrases, and sentences, insufficient information was available to discriminate formants and their transitions. Single words could be recognized but understanding of running speech was not possible for the first implantees. Research following the first implantation of single channel (Djourno and Eyries, 1957) and a multichannel device (Doyle et al., 1963) showed that cochlear implants should be multichannel devices inserted into scala tympani (Clark, Dowell, et al., 1984; Clark, Tong, et al., 1984; House and Berliner, 1982; House and Edgerton, 1982; Simmons, Dent, and Van Compernolle, 1986; Simmons, Mathews, Walker, and White, 1979). Initial results were improved by emphasizing the mid and high frequency cues (Edgerton and Brimacombe, 1984). A similar system was implemented at Vienna (Hochmair et al., 1979). The system included gain compression, followed by frequency equalization. While single words could be recognized, open-set speech recognition was not possible in any of the single channel devices.

Multichannel coding strategies were developed to model the tonotopic organization of the cochlea. For the selection of number of channels, the results from the vocoders were used. However, early attempts to stimulate at all channels simultaneously resulted in unpredictable changes in loudness (Shannon, 1981). To avoid interaction between channels, electrical stimuli were presented as pulses and non-simultaneously at neighboring electrode contacts (Shannon, 1981, 1983, 1985). While early coding strategies suffered from channel interactions by stimulating at neighboring electrodes, novel strategies were tested to overcome existing limitations in stimulation strategies and resulted to the introduction of the continuous interleaved sampler (CIS) coding strategy (Lawson, Wilson, & Finley, 1993; Wilson, 1997; Wilson et al., 1991; Wilson, Finley, Lawson, Wolford, and Zerbi, 1993).

The continuous interleaved sampler (CIS) coding strategy is in widespread use amongst current cochlear implants (Wilson and Dorman, 2008). CIS processing utilizes band pass filters, then compress the envelope signals extracted from these filters to map the large dynamic range up to 100 dB to the smaller range of electrically evoked hearing, which is about 10 dB (Wilson and Dorman, 2008). The outputted trains of electrical pulses are then sent to tonotopically placed electrodes to mimic the frequency mapping of a normal cochlea (Wilson and Dorman, 2008; Flint, 2010). The amplitude of the transmitted pulse is determined by the amplitude of the original pulse from the acoustic signal (Flint, 2010). Cochlear implants seek to independently stimulate neuron sites to allow for the best speech perception, though studies suggest that no more than 4-8 independent sites can be stimulated in many electrode designs (Fishman, 1997; Wilson, 1997; Kiefer et al., 2000; Garnham et al., 2002). The CIS strategy attempts to avoid the issue of electrical interference and stimulate more independent areas through transmitting the pulse trains across electrodes in an interleaved non-simultaneous manner, such that there is a temporal offset between stimuli (Wilson et al., 1991 and Wilson and Dorman, 2008). Additionally, the brief pulses are transmitted at a high rate (typically about 1500 pulses/s), which allows for the preservation of temporal fine structure of the acoustic signal (Somek, 2006; Wilson and Dorman, 2008).

While the pattern of delivering the electrical pules at each contact of the cochlear implant electrode is on part of the coding strategy, the selection of the acoustic information to be presented constitutes the second part of the coding strategy.

The selection algorithms include Spectral Peak Extraction (SPEAK) coding and Advanced Combination Encoder (ACE) coding strategy and its variations. SPEAK sends the incoming signal through a bandpass filter, and then takes approximately 6 ms to scan the output of those frequency filters and selects for transmission to the cochlea the 6 filters with the most energy, that is the frequencies with the most amplitude or the highest spectral peaks (Somek, 2006). Electrodes are then stimulated in a basal to apical direction. About 6 to 8 electrodes are usually stimulated, but the more electrodes stimulated, the slower the rate of transmission of the outgoing signal. The Advanced Combination Encoder (ACE) coding strategy is very similar to SPEAK except it utilizes higher rates of stimulus, as does CIS, than with the low rate SPEAK strategy (Rubinstein, 2004; Wilson and Dorman, 2008). It was designed to include the benefits of SPEAK with a high rate CIS. ACE provides for the transmission of more information to the auditory nerve compared to SPEAK. Pulse rates of 500 to 3500 pulses per second, and a maxima range from 1 to 20 electrodes stimulated simultaneously can be achieved (Flint, 2010).

The auditory sensation that is used to order sound along a scale from quiet to loud is defined as loudness. It is a subjective sensation, which correlates with sound intensity. Loudness is a subjective measure and changes with frequency. The neurophysiological correlates for loudness are the rate of action potentials at a nerve fiber and the recruitment, the number of neurons, which are exited at the same time. The ears of a normal hearing subject can cover a 120 dB range of sound levels. Hearing impairment decreases this range drastically and in cochlear implant users the range is typically less than 20 dB.

The decrease of the range over which loudness can be coded can be attributed to two facts, the loss of the loss spontaneously active fibers, and the all-or nothing recruitment of auditory nerve fibers in the current field during electrical stimulation. Auditory nerve fibers with low spontaneous activity require higher sound levels for stimulation. Combined with the auditory nerve fibers that respond to soft sounds the entire population of fibers can encode the 120 dB range in sound levels. Loss of a population of nerve fibers or the synchronous discharge of neurons at the same time limits the dynamic range of artificial stimulation.

Pulse repetition rates that are faster than the recovery of an auditory neuron after an action potential occurred result in more stochastic activity of the nerve. Similar stochastic neural activity can be seen at the threshold of stimulation. The latter point is important for this patent because the novel coding strategy allows the reduction of the current such that stochastic firing pattern occurs. The rate increase is not achieved by the increase in the current amplitude, but by the pulse generator.

Biophysical properties of the cochlea and its solutions determine the current spread during electrical stimulation. For monopolar stimulation, one of the electrodes is placed in the cochlea and the reference electrode is located outside the cochlea, interaction occurs not only for close neighboring electrodes. The current spreads for about 3 mm along the cochlea (the equivalent of about 3 electrode contacts). Multi-polar stimulation paradigms may offer some opportunities to focus the current field to the target structures or to stimulate at areas between two electrode contacts. The price for the selectivity is an increase in power consumption and the simultaneous use of multiple electrode contacts. It is not surprising that multipolar stimulation did not result in drastic improvements in patient performance.

To avoid interactions between neighboring electrodes, contemporary coding strategies use interleaved stimulation paradigms. Amplitude-modulated trains of electrical pulses at repetition rates at about, and well above 300 Hz, are used to encode the acoustical information. It has been argued that high repetition rates, which are well above 300 Hz, better reproduce the fine structure of the auditory signal and that more stochastic activity can be seen that increases the range over which the current level can be changed.

Therefore, a heretofore unaddressed need exists in the art to address the aforementioned deficiencies and inadequacies.

SUMMARY OF THE INVENTION

In one aspect, the invention relates to a method for neuromodulation device coding for stimulation of a patient.

In one embodiment, the method includes (a) identifying a pattern of a sensory signal; (b) retrieving one or more digital representations of a neural response corresponding to the identified pattern from a neural code library, wherein the neural code library comprises a plurality of digital representations of neural responses of neural units corresponding to each pattern; (c) selecting one or more neural units of a patient to be stimulated by a neuromodulation device associated with the patient based on the retrieved one or more digital representations of a neural response pattern; and (d) stimulating the selected neural units of the patient.

Further, the foregoing steps (a)-(d) are repeated consecutively for each pattern of the sensory signal.

In one embodiment, the method may comprise optimizing the selection of the units for stimulation optimization based on feedback from the patient.

In one embodiment, the nueromodulation device is implanted in the patient.

In one embodiment, the neuromodulation device is a cochlear implant implanted in the patient.

In one embodiment, the sensory signal is an acoustic signal. In one embodiment, the step of identifying the pattern of the sensory signal is performed with a speech recognition algorithm.

In one embodiment, the step of retrieving one or more digital representations of a neural response corresponding to the identified pattern from the neural code library is performed with a stochastic model including but not limited to a Hidden Markov Model (HMM).

In one embodiment, the plurality of digital representations of neural responses of neural units are derived from the measured neural responses of neural units in a normal functioning animal. The normal functioning animal includes, but is not limited to, a normal hearing animal.

In one embodiment, each neural unit is an identifiable and stable single unit in at least one of the inferior colliculus, cochlear nucleus, auditory nerve, haptics, brainstem, and midbrain of the normal hearing functioning.

In one embodiment, the neural responses of neural units of the normal functioning animal are acquired from neural recordings in the neural units when each pattern is played to the normal functioning animal at a plurality of frequencies.

In one embodiment, each neural response pattern contains a sequence of neural responses of a corresponding neural unit at its corresponding best frequency to the identified pattern.

In one embodiment, the neural response of each neural unit of the normal hearing animal comprises a train of action potentials generated in the neural unit of the normal functioning animal in response to the receipt of the acoustical pattern.

In one embodiment, the selected neural units of the patient are simulated with electrical pulses that are coincident with the trains of action potentials generated in the corresponding neural units of the normal functioning animal in response to the receipt of the identified pattern.

In one embodiment, the pattern is a segment or a frame of the sensorysignal. In one embodiment, the pattern comprises a phoneme, a syllable, a word, words, or a combination thereof.

In another aspect, the invention relates to a method for cochlear implant coding for stimulation of a patient. In one embodiment, the method includes (a) identifying an acoustical pattern of an acoustical signal; (b) retrieving a set of neural response patterns corresponding to the identified acoustical pattern from a neural code library, wherein the neural code library comprises neural responses of neural units of at least one normal hearing animal to each acoustical pattern at a plurality of frequencies, where each neural response pattern contains a sequence of neural responses of a corresponding neural unit at its corresponding best frequency to the identified acoustical pattern; (c) selecting units to be stimulated according to electrode contacts of a cochlear implant implanted in the patient and corresponding neural response patterns from the retrieved set of neural response patterns; and (d) applying pulses according to the selected neural response patterns to the electrodes of the cochlear implant to stimulate the selected units of the patient for sensing the acoustical pattern. Further, the foregoing steps (a)-(d) are repeated consecutively for each acoustical pattern of the acoustical signal.

In one embodiment, the method may comprise optimizing the selection of the units for stimulation optimization based on feedback from the patient.

In yet another aspect, the invention relates to a system for cochlear implant coding for stimulation of a patient. In one embodiment, the system has a neural code library, a sensory device, an analyzer, a processing device, and a transmitting device.

The neural code library comprises a plurality of digital representations of neural responses of neural units of at least one normal hearing animal, wherein each of the plurality of digital representations of neural responses corresponds to one of a plurality of digital representations of acoustic patterns.

The sensory device is configured to detect an acoustical signal. In one embodiment, the sensory device comprises one or more microphones.

The analyzer is in communication with the sensory device via a wired or cable connection, or a wireless connection, and is configured to identify one of the digital representations of acoustic patterns in the neural code library in response to the receipt of the acoustic signal.

The processing device is in communication with the neural code library and the analyzer via a wired or cable connection, or a wireless connection and configured, for each identified acoustical pattern, to retrieve the digital representations of neural responses of neural units corresponding to the identified acoustic pattern from the neural code library, and select one or more neural units of a patient to be stimulated by a cochlear implant implanted in the patient.

The transmitting device is in communication with the processing device and the cochlear implant via a wired or cable connection, or a wireless connection, and configured, for each identified acoustical pattern, to stimulate the selected one or more neural units of the patient for sensing the acoustical signal.

In one embodiment, the digital representations of the neural responses include data for each of a plurality of frequencies.

In one embodiment, each neural response pattern contains a sequence of neural responses of a corresponding neural unit at its corresponding best frequency to the identified acoustic pattern.

In one embodiment, each neural unit is an identifiable and stable single unit in at least one of the inferior colliculus, cochlear nucleus, auditory nerve, brainstem, and midbrain of the normal hearing animal.

In one embodiment, the neural responses of neural units of the normal hearing animal are acquired from neural recordings in the neural units when each acoustical pattern is played to the normal hearing animal at the plurality of frequencies.

In one embodiment, the neural response of each neural unit of the normal hearing animal comprises a train of action potentials generated in the neural unit of the normal hearing animal in response to the receipt of the acoustical pattern.

In one embodiment, the selected one or more neural units of the patient are stimulated with electrical pulses that are coincident with the trains of action potentials generated in the corresponding neural units of the normal hearing animal in response to the receipt of the acoustical pattern.

In one embodiment, the acoustical pattern is a segment or a frame of the acoustical signal. In one embodiment, the acoustical pattern comprises a phoneme, a syllable, a word, words, or a combination thereof.

In one embodiment, the electrodes of the cochlear implant comprise an electrode array with multiple electrode contacts.

In one embodiment, the transmitting device is a wireless transmitting device. In one embodiment, the wireless transmitting device is a Bluetooth wireless transmitter.

In a further aspect, the invention relates to a method for playing an acoustical signal to a patient having a cochlear implant implanted.

In one embodiment, the method includes selecting an acoustical signal which the patient wants to listen to; looking up a neural code library, wherein the neural code library comprises a plurality of digital representations of neural responses of neural units of at least one normal hearing animal, wherein each of the plurality of digital representations of neural responses corresponds to one of a plurality of digital representations of acoustic signals and comprises a neural response pattern; if the selected acoustical signal exists in the neural code library, selecting one or more neural units of a patient to be stimulated by a cochlear implant implanted in the patient; and stimulating the selected one or more neural units of the patient for listening to the acoustical signal.

In one embodiment, the method further comprises optimizing the selection of the units for stimulation optimization based on feedback from the patient.

In one embodiment, each neural unit is an identifiable and stable single unit in at least one of the inferior colliculus, cochlear nucleus, auditory nerve, brainstem, and midbrain of the normal hearing animal.

In one embodiment, the neural responses of neural units of the normal hearing animal are acquired from neural recordings in the neural units when each acoustical signal is played to the normal hearing animal at a plurality of frequencies.

In one embodiment, each neural response pattern comprises a train of action potentials generated in a corresponding neural unit of the normal hearing animal in response to the receipt of the acoustical signal.

In one embodiment, the selected one or more neural units of the patient are stimulated with electrical pulses that are coincident with the trains of action potentials generated in the corresponding neural units of the normal hearing animal in response to the receipt of the acoustical signal.

In yet a further aspect, the invention relates to a system for playing an acoustical signal to a patient having a cochlear implant implanted.

In one embodiment, the system includes a neural code library comprising a plurality of digital representations of neural responses of neural units of at least one normal hearing animal, wherein each of the plurality of digital representations of neural responses corresponds to one of a plurality of digital representations of acoustic patterns and comprises a neural response pattern; a processing device in communication with the neural code library, configured to look up the neural code library, and if the selected acoustical signal exists in the neural code library, select one or more neural units of a patient to be stimulated by a cochlear implant implanted in the patient; and a transmitting device in communication with the processing device and the cochlear implant, configured to stimulate the selected one or more neural units of the patient for listening to the acoustical signal.

In one embodiment, each neural unit is an identifiable and stable single unit in at least one of the inferior colliculus, cochlear nucleus, auditory nerve, brainstem, and midbrain of the normal hearing animal.

In one embodiment, the neural responses of neural units of the normal hearing animal are acquired from neural recordings in the neural units when each acoustical pattern is played to the normal hearing animal at a plurality of frequencies.

In one embodiment, each neural response pattern comprises a train of action potentials generated in a corresponding neural unit of the normal hearing animal in response to the receipt of the acoustical signal.

In one embodiment, he selected one or more neural units of the patient are stimulated with electrical pulses that are coincident with the train of action potentials generated in the neural unit of the normal hearing animal in response to the receipt of the acoustical signal.

In one embodiment, the electrodes of the cochlear implant comprise an electrode array with multiple electrode contacts.

In one embodiment, the processing device is in communication with the neural code library via a wired or cable connection, or a wireless connection.

In one embodiment, the transmitting device is in communication with the processing device and the cochlear implant via a wired or cable connection, or a wireless connection.

In one embodiment, the transmitting device is a wireless transmitting device. In one embodiment, the wireless transmitting device is a Bluetooth wireless transmitter.

In one aspect of the invention, a method for neuromodulation device coding for stimulation of an epilepsy patient may be used in connection with a closed loop deep brain stimulator. In one embodiment, the method may be implemented according to the following steps: identifying a pattern of pathological neural activity that heralds the beginning of epileptic activity; retrieving one or more digital representations of a neural response corresponding to a therapeutic neural response for the identified pathological neural activity from a neural code library, wherein the neural code library comprises a digital representation of appropriate therapeutic neural responses that correspond to a library recorded from an animal, or a library algorithmically reconstructed to mimic the library based on the library recorded from an animal; selecting one or more neural units of a patient to be stimulated by the deep brain stimulator associated with the patient based on the retrieved one or more digital representations of a neural response pattern; and using the deep brain stimulator to stimulate the selected neural units of the patient.

In another aspect of the invention, a method for neuromodulation device coding for stimulation of a patient may be used in connection with a deep brain stimulator. In one embodiment, the method may be implemented according to the following steps: either the patient or the neuromodulation device selects a desired neural signal from a neural code library; retrieving one or more digital representations of a neural response corresponding to the identified pattern from a neural code library, wherein the neural code library comprises a digital representations of a neural response of neural units corresponding to each pattern; selecting one or more neural units of a patient to be stimulated by the deep brain stimulator associated with the patient based on the retrieved one or more digital representations of a neural response pattern; and using the deep brain stimulator to stimulate the selected neural units of the patient.

In yet another aspect of the invention, a method for neuromodulation device coding for stimulation of a patient may be used in connection with a spinal cord stimulator. In one embodiment, the method may be implemented according to the following steps: either the patient or the neuromodulation device selects a desired neural signal from a neural code library; retrieving one or more digital representations of a neural response corresponding to the identified pattern from a neural code library, wherein the neural code library comprises a digital representations of a neural response of neural units corresponding to each pattern; selecting one or more neural units of a patient to be stimulated by the deep brain stimulator associated with the patient based on the retrieved one or more digital representations of a neural response pattern; and using the spinal cord stimulator to stimulate the selected neural units of the patient.

In a further aspect of the invention, a method for neuromodulation device coding for stimulation of a patient may be used in connection with a retinal implant. In one embodiment, the method may be implemented according to the following steps: a visual signal is analyzed by a computer vision algorithm which is used to identify and select items from a scene based upon the patient's preselected scene complexity parameters; the algorithm retrieves one or more digital representations of the scene items corresponding to the identified pattern from a neural code library, wherein the neural code library comprises digital representations of neural response of neural units corresponding to each pattern; selecting one or more neural units of a patient to be stimulated by the retinal implant associated with the patient based on the retrieved one or more digital representations of a neural response pattern; and using the retinal implant to stimulate the selected neural units of the patient.

These and other aspects of the invention will become apparent from the following description of the preferred embodiment taken in conjunction with the following drawings, although variations and modifications therein may be affected without departing from the spirit and scope of the novel concepts of the invention.

BRIEF DESCRIPTION OF THE DRAWINGS

The patent or application file contains at least one drawing executed in color. Copies of this patent or patent application publication with color drawing(s) will be provided by the Patent and Trademark Office upon request and payment of the necessary fee.

The accompanying drawings illustrate one or more embodiments of the invention and, together with the written description, serve to explain the principles of the invention. Wherever possible, the same reference numbers are used throughout the drawings to refer to the same or like elements of an embodiment.

FIG. 8 is a table listing the correct words presented during the testing according to one embodiment of the invention. It also shows the possible selections for the test subject and which decisions were made. The data of 4 test subjects are shown.

FIG. 9 is a table listing the number of correct and wrong selections for all subjects tested even if only partial data sets were available, according to one embodiment of the invention.

DETAILED DESCRIPTION OF THE INVENTION

Figure 1:
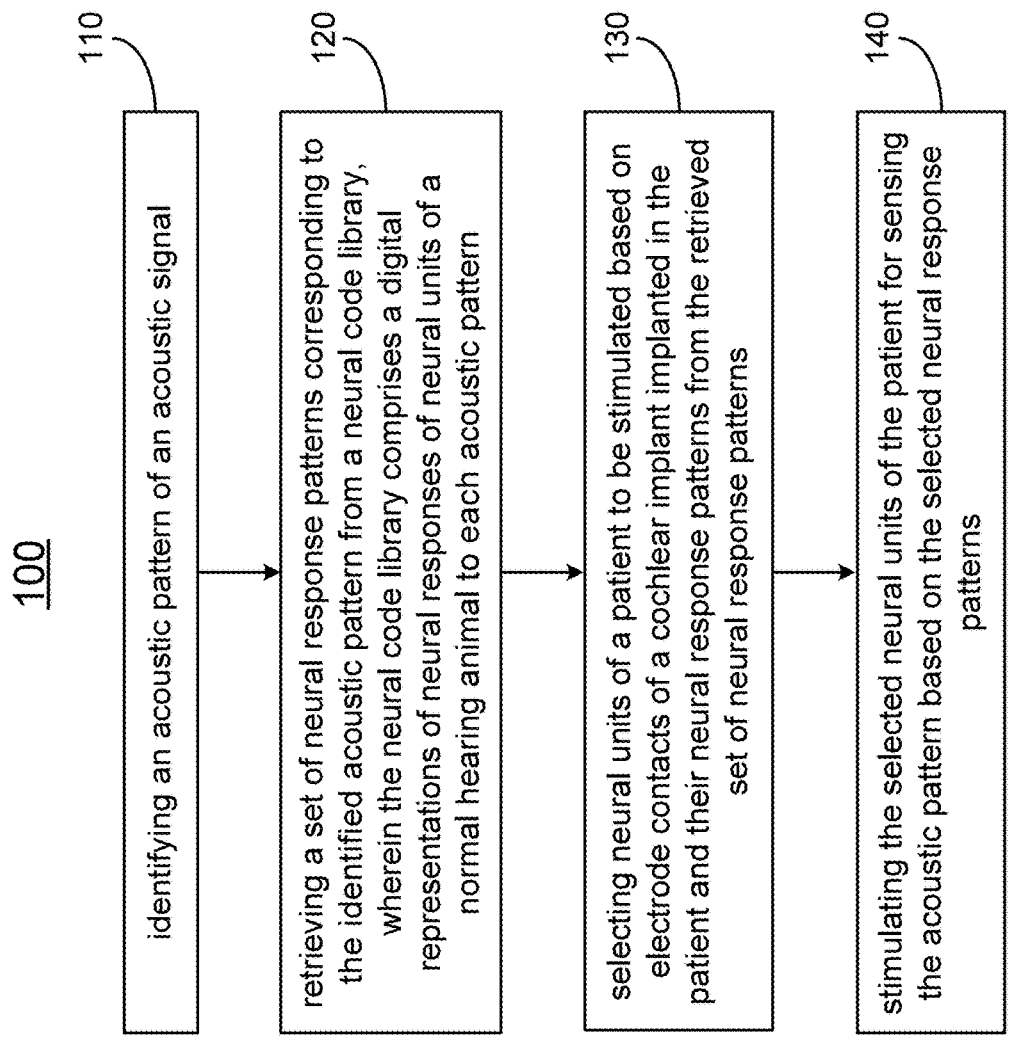
FIG. 1 shows schematically a flowchart for cochlear implant coding for stimulation of a patient according to one embodiment of the invention.

The invention will now be described more fully hereinafter with reference to the accompanying drawings, in which exemplary embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

It will be understood that, as used in the description herein and throughout the claims that follow, the meaning of "a", "an", and "the" includes plural reference unless the context clearly dictates otherwise. Also, it will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the invention.

Furthermore, relative terms, such as "lower" or "bottom" and "upper" or "top," may be used herein to describe one element's relationship to another element as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower", can therefore, encompasses both an orientation of "lower" and "upper," depending of the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

It will be further understood that the terms "comprises" and/or "comprising," or "includes" and/or "including" or "has" and/or "having", or "carry" and/or "carrying," or "contain" and/or "containing," or "involve" and/or "involving, and the like are to be open-ended, i.e., to mean including but not limited to. When used in this disclosure, they specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

As used herein, the phrase "at least one of A, B, and C" should be construed to mean a logical (A or B or C), using a non-exclusive logical OR. It should be understood that one or more operations within a method is executed in different order (or concurrently) without altering the principles of the invention.

As used herein, the term "action potentials" refer to the electric response of nerve fibers or muscle tissues to its stimulation such as electrical stimuli, optical stimuli, and/or acoustic click stimuli. The action potentials are considered as the traveling signals of nerves and the localized changes that contract muscle cells responsive to the stimulation. Compound action potentials are the summation of individual action potentials from single neurons.

As used herein, the term "nerve fiber" refers to a portion of the neuron, namely the axon, which carries action potentials from one end of the neuron to the other. The cochlear nerve fibers originate from neurons of the spiral ganglion and project peripherally to cochlear hair cells and centrally to the cochlear nuclei (cochlear nucleus) of the brain stem. They mediate the sense of hearing.

The term "cochlea," as used herein, refers to a spiral-shaped cavity of the inner ear that resembles a snail shell and contains nerve endings essential for hearing. The cochlea includes three fluid-filled chambers: scala tympani and scala vestibuli (both of which contain perilymph), and scala media (which contains endolymph). The scala tympani and the scala vestibuli are contiguous with each other, merging at the tip of the snail shell, the helicotrema. The stapes transmits vibrations to the fenestra ovalis (oval window) on the outside of the cochlea, which vibrates the perilymph in the scala vestibuli. This in turn vibrates the endolymph in the scala media, thus causing movements of the hair bundles of the hair cells, which are acoustic sensor cells that convert vibration into electrical potentials.

The term "cochlear implant", as used herein, refers to a device that is placed into the cochlea to provide sound perception for deaf individuals.

Embodiments of the invention are illustrated in detail hereinafter with reference to accompanying drawings. It should be understood that specific embodiments described herein are merely intended to explain the invention, but not intended to limit the invention. In accordance with the purposes of this invention, as embodied and broadly described herein, this invention, in certain aspects, relates to a novel coding strategy, i.e., methods and systems for neuromodulation device coding with trans-species libraries, and more particularly to systems and methods for cochlear implant coding with trans-species neural code libraries.

Improvement of cochlear implant performance over the last decades is based on improved coding of the acoustic information. Although the increase of performance has recently plateaued, performance can be further enhanced with the novel coding strategy. In certain embodiments, the novel coding strategy uses speech recognition algorithms to identify an acoustic pattern of speech (i.e., an acoustic signal) and matches the acoustic pattern of speech with neural responses, which were recorded from the auditory nerve, the cochlear nucleus, or the inferior colliculus of normal hearing animals (or normal functioning animals). The neural response patterns are recorded from different sites (neural units or neurons) along the cochlea to match the tonotopic organization of the auditory system. The neural stimulation patterns are used to stimulate the auditory nerve with the cochlear implant for a cochlear implant user (patient). Once the speech recognition algorithm has identified an acoustic pattern such as phoneme, syllable, or word, it matches this acoustic pattern with a basic set of stimulation patterns. Since for each acoustic pattern, several neural responses exist in the neural code library, ordered by the tonotopic site along the cochlea in which they were recorded, a "self learning" model such as but not limited to Hidden Markov Model (HHM) is used to optimize the distribution of the patterns along the different contacts of the electrode array. Among other things, the novel coding strategy provides more natural patterns of stimulation, decreases the average stimulation rate by about a factor of about 10, has fixed stimulation currents close to stimulation threshold, provides more stochastic firing pattern of the neurons and increases the number of independent channels for speech coding.

Among other unique features, the invented coding strategy utilizes a neural code library, i.e., a trans-species library. The neural code library comprises neural responses of neural units of at least one normal functioning/hearing animal to each acoustic pattern at a plurality of frequencies. In certain embodiments, the neural responses of neural units of the normal functioning/hearing animal corresponding to each acoustic pattern are represented by a plurality of digital representations in the neural code library. Each of the plurality of digital representations represents a neural response pattern of a corresponding neural unit. The plurality of digital representations of neural responses of neural units are derived from the measured neural responses of neural units in the normal functioning/hearing animal. To create the library, in certain embodiments, neural responses are recorded from neurons (neural units) in the inferior colliculus, the cochlear nucleus, or the auditory nerve of the normal hearing animal while phonemes, syllables, and words are played to the ears of the normal hearing animal. Generally, a neural unit is an identifiable and stable single unit in at least one of the inferior colliculus, cochlear nucleus, auditory nerve, brainstem, and midbrain of the normal hearing animal. Neural recordings are done with single tungsten, glass electrodes, or the like. After surgically gaining access to the target structure, the recording electrode is inserted into the tissue and is advanced until contact with a single neuron has been established. The best frequency for each of the neurons is determined before the responses to the selected phonemes, syllables, and words are recorded. The best frequency of a neural unit is a frequency for pure tone stimulation that needs a lowest sound level to evoke a neural response in the corresponding unit. By knowing the best frequency of the location, the responses can be frequency matched with each of the contacts of the cochlear implant electrode. The neural response of each neural unit of the normal hearing animal comprises a train of action potentials generated in the neural unit of the normal hearing animal in response to the receipt of the acoustic pattern.

The neural code library or trans-species library may be stored in local computers, servers, or cloud dives on the internet. Further, more neural response patterns can be added into the neural code library from tine to time. The more the neural response patterns in the neural code library, the more accurate the neural stimulations.

Referring to FIG. 1, a method (flowchart) 100 for cochlear implant coding for stimulation of a patient is schematically shown according to one embodiment of the invention. In the exemplary embodiment, the method includes the following steps: at first, an acoustic pattern of an acoustic signal is identified at step 110.

In certain embodiments, the acoustic pattern is a segment or a frame of the acoustic signal. In certain embodiments, the acoustic pattern comprises a phoneme, a syllable, a word, words, or a combination thereof. In some embodiments, the system continuously records the acoustic information (signal) and converts the acoustic signal into a track of voltage values obtained from, for example, a microphone. Overlapping frames are acquired. Hereby, each frame is continuously shifted every 10 ms or optimized otherwise.

In certain embodiments, speech recognition algorithms are utilized to identify an acoustic pattern of the acoustic signal and matches the acoustic pattern of the acoustic signal with neural responses. For example, a Fast Fourier Transform of the acoustic signal provides the acoustic signal in the frequency domain and allows comparing the pattern of the speech signal with patterns stored in the neural code library.

Speech recognition algorithms are based on three approaches, the acoustic phonetic, the pattern recognition, and the artificial intelligence approach. Acoustic phonetic approaches try to find speech sounds and label these sounds. Pattern matching involves two essential steps, pattern training and pattern comparison. A speech pattern representation can be in the form of a speech template or a statistical model to be applied to either segments shorter than a word, words, or sentences. Today, pattern recognition is the most common method used in speech recognition. Artificial intelligence to recognize speech relies on elements found in the phonetic and the pattern recognition approaches. All approaches rely on the ability to extract features from the acoustic signal that can be matched with features found in speech and use a parametric representation of speech rather the time waveform itself To extract features from the signal, method such as the principal component analysis (PCA), linear discriminant analysis (LDA), independent component analysis (ICA), linear predictive coding (LPC) (Davis, 1986; Durand and Pibarot, 1995; Erickson and D'Alfonso, 2002; Kob and Neuschaefer-Rube, 2002; Gaubitch et al., 2006; Stephens and Holt, 2011; Wang et al., 2011), cepstral analysis, Mel-frequency scale analysis, filter bank analysis, Mel-frequency cepstrum (MFFCs), kernel based feature extraction method, wavelet analysis, dynamic feature extraction, (LPC and MFCC) spectral subtraction cepstral mean subtraction, RASTA filtering, or an integrated phoneme subspace method.

Once the acoustic pattern, such as a word, is recognized, it will be used to retrieve corresponding recorded neural response patterns from the midbrain, brain stem, or the auditory nerve of an animal in the neural code library. In certain embodiments, the recorded neural response patterns are represented by the digital representations in the neural code library.

At step 120, a set of neural response patterns (i.e., one or more digital representations) corresponding to the identified acoustic pattern is retrieved from the neural code library. Each neural response pattern contains a sequence of neural responses of a corresponding neural unit at its corresponding best frequency to the acoustic pattern. Since for each acoustic pattern, several neural responses exist in the neural code library, ordered by the tonotopic site along the cochlea in which they were recorded, a stochastic model such as a Hidden Markov Model (HHM) is used to optimize the distribution of the patterns along the different contacts of the electrode array. That is, the stimulation pattern in the neural code library is optimally matched with the contacts of the cochlear implant electrode for any given patient. Number of contacts used is optimized for speech recognition.

At step 130, one or more neural units (neurons) of a patient to be stimulated are selected based on electrode contacts of a cochlear implant implanted in the patient and their neural response patterns from the retrieved set of neural response patterns. For example, for a cochlear implant with 16 electrodes, 16 neural units of the patient are selected. The frequency is matched to the best frequency of each contact of the cochlear implant, which determined for each patient.

Figure 3:
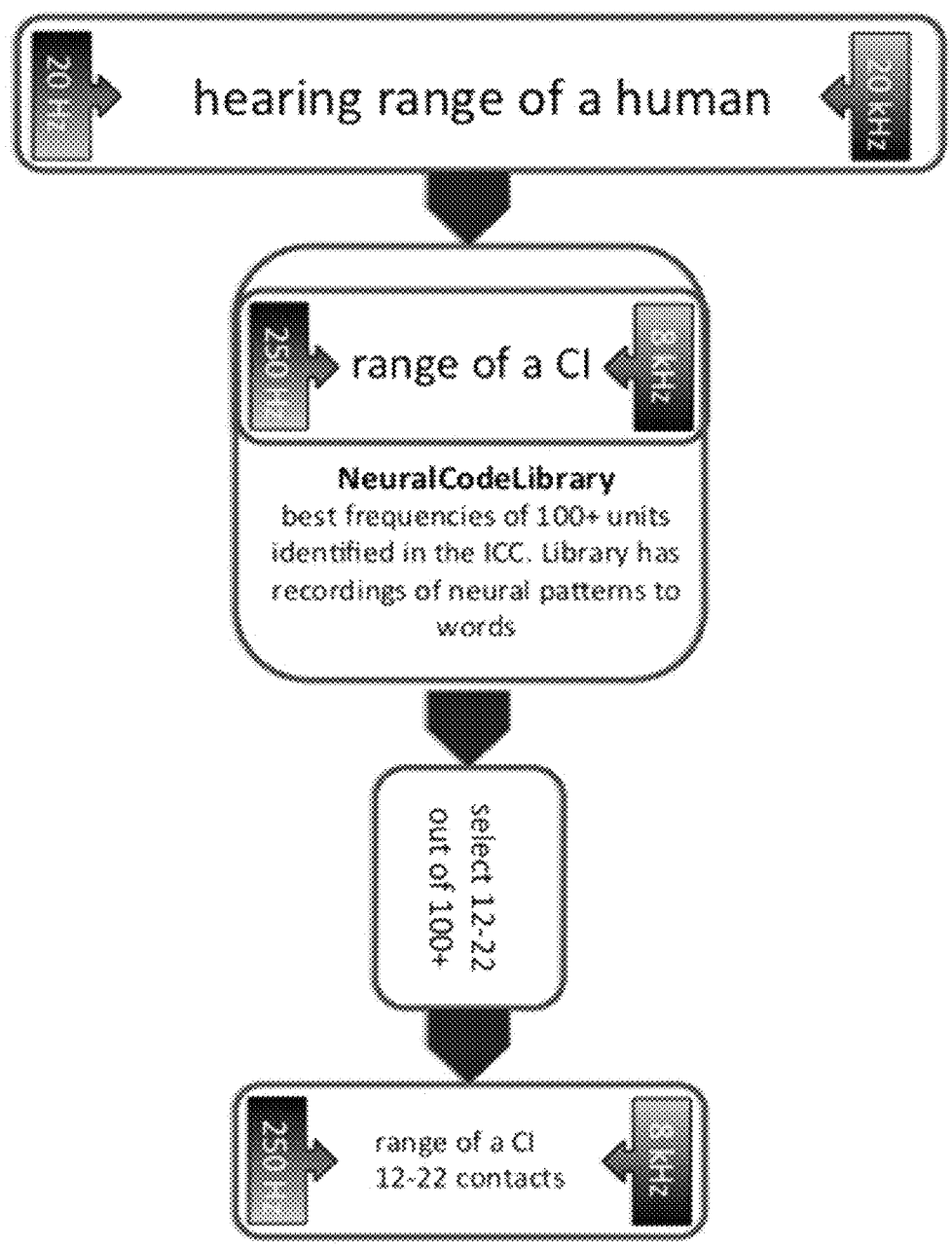
FIG. 3 shows schematically frequency mapping in the cochlear implant coding for stimulation of a patient according to one embodiment of the invention.
Figure 4:
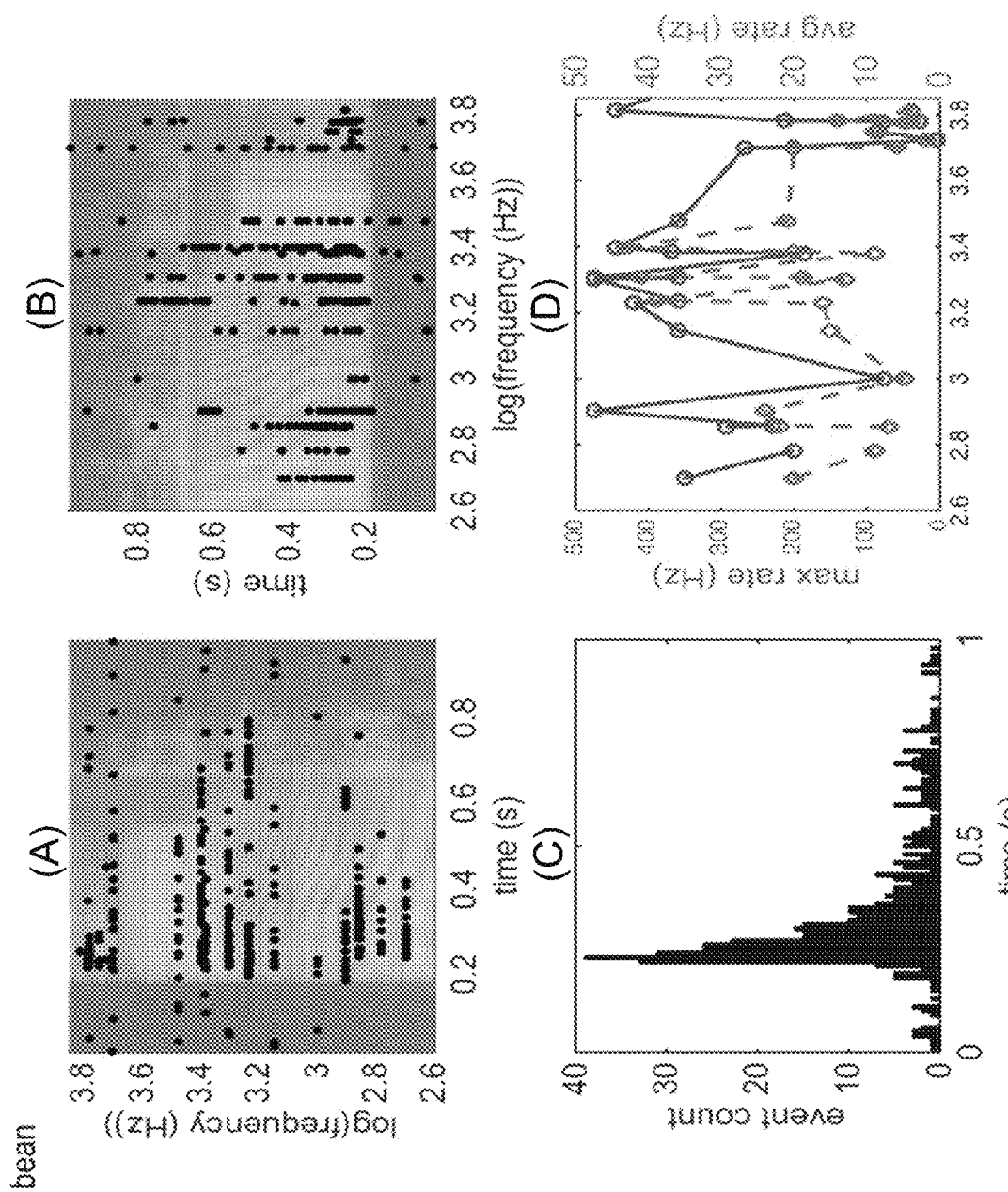
FIGS. 4-7 show preliminary experimental data of the cochlear implant coding for the stimulation for few selected words "bean", "bomb", "shirt" and tough", respectively, according to embodiments of the invention. In panel (A), the y-axis of the spectrogram represents the log-frequencies and the x-axis of the spectrogram represents the time; in panel (B), the y-axis of the spectrogram represents the time and the x-axis of the spectrogram represents the log-frequency of the acoustical signal. The color is a measure for the magnitude, where the darker colors are for larger magnitudes, and the brighter colors such as yellow and white show low magnitudes. The black dots show corresponding sequences of action potentials that were recorded in the guinea pig inferior colliculus, while the word was played to the animal's ear. The panel (C) shows the accumulated number of action potentials of the panel (A) in a 10 ms time interval. The panel (D) shows the average rate of action potentials for each of the channels (green) and a maximum rate, which was calculated from the shortest time interval between successive action potentials in each channel.
Figure 5:
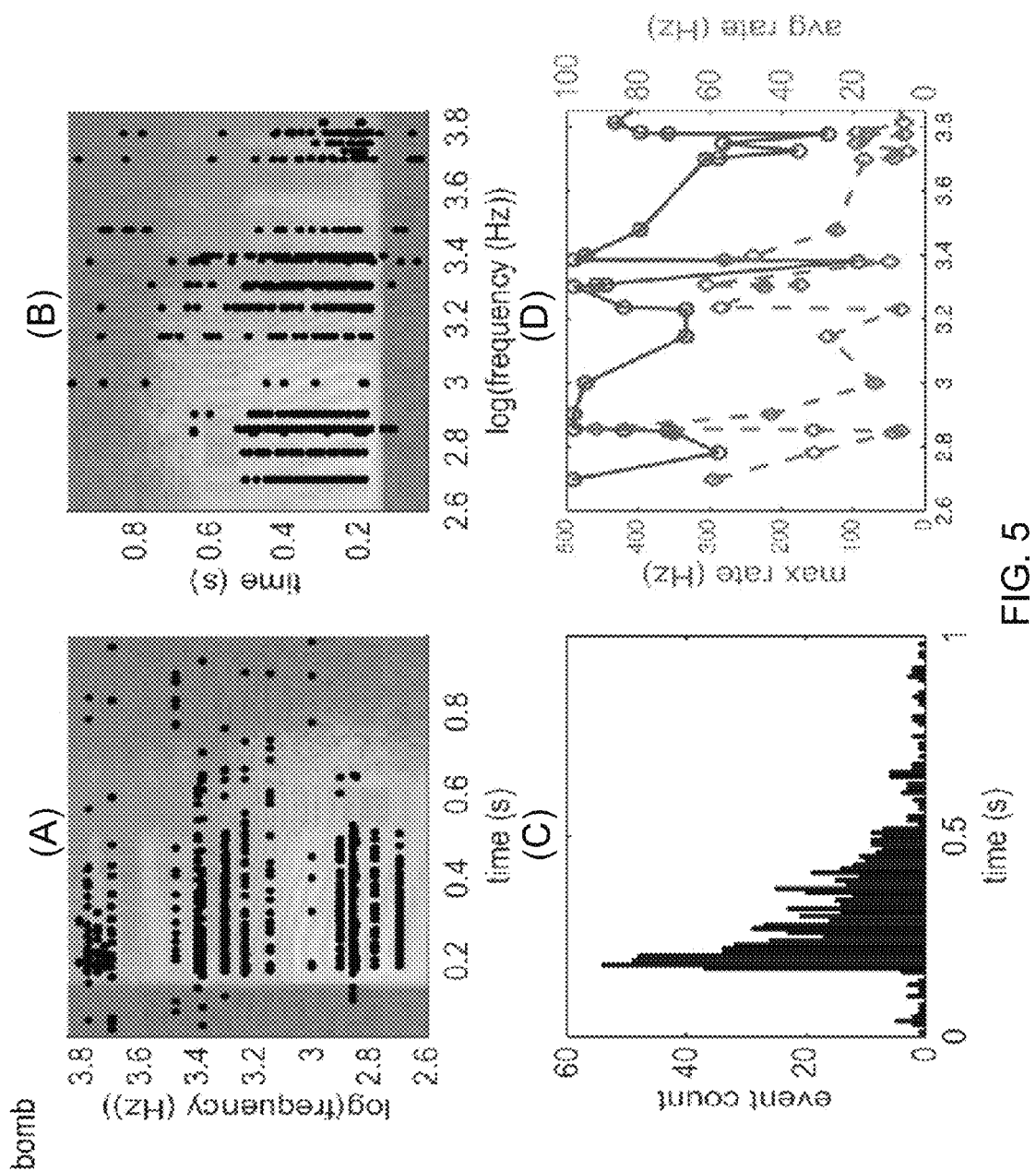
Figure 6:
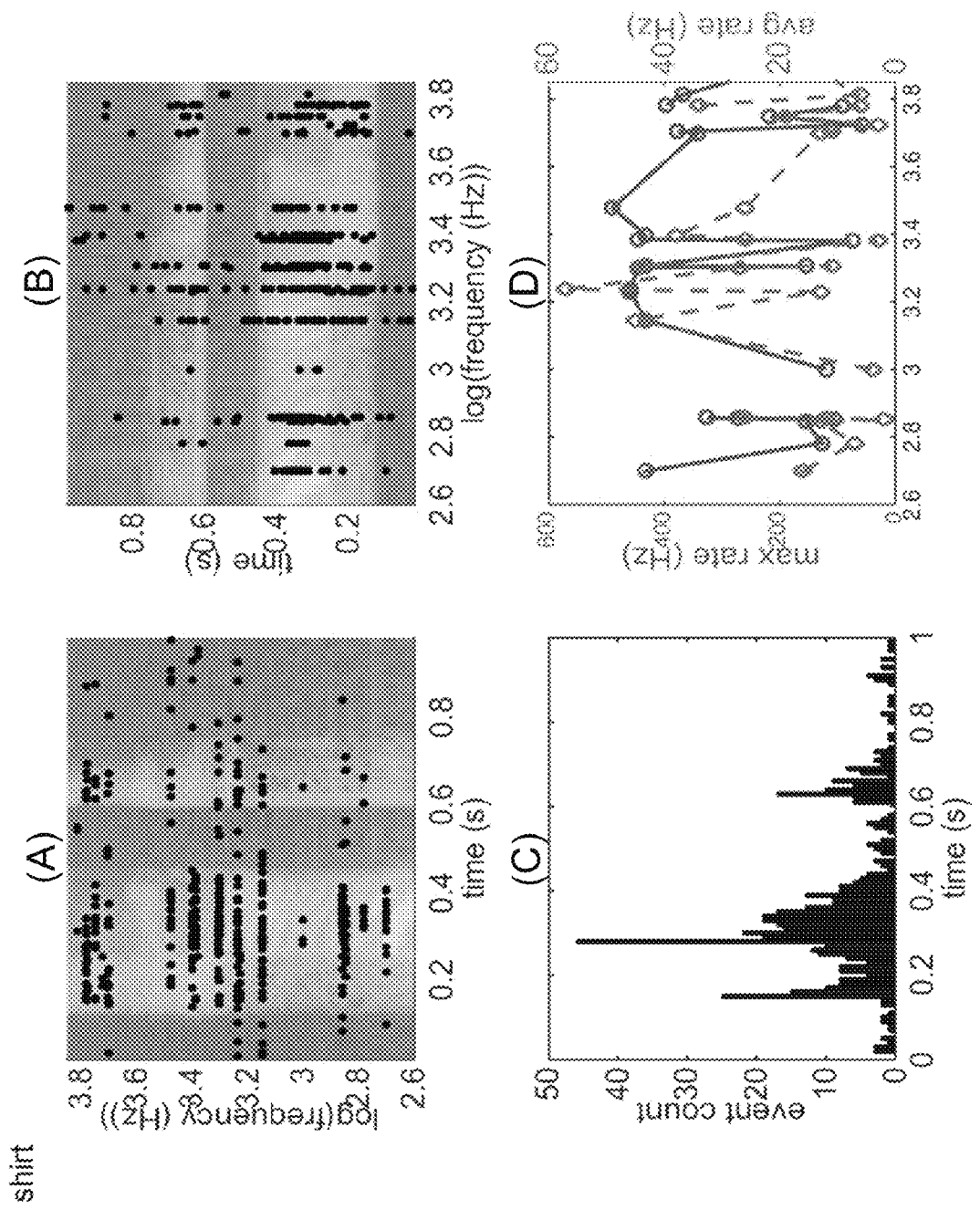
Figure 7:
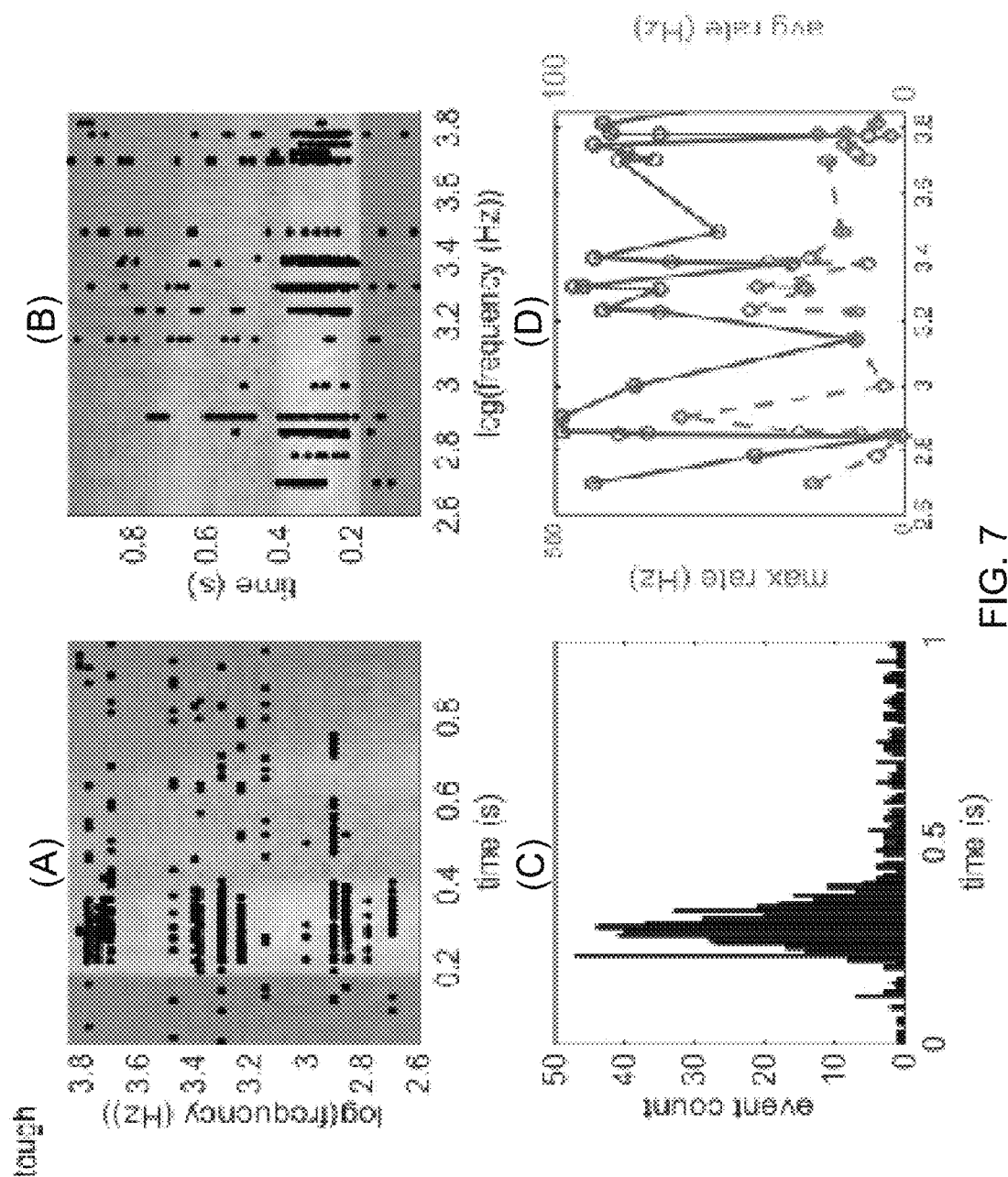

FIG. 3 shows schematically frequency mapping from a normal hearing range of 20 Hz to 20 KHz of a human to a range of 250 Hz to 8 kHz for a cochlear implant and the selection of the neural units of the patient for stimulation in the cochlear implant coding method according to one embodiment of the invention. In this exemplary embodiment, the neural code library contains recordings of neural response patterns of a normal hearing animal to words, where the best frequencies of more then 100 units are identified in the cochlear implant coding, which are in the range of 20 Hz to 20 kHz. However, the electrode contacts of a cochlear implant, where the neural units at the electrode contacts are stimulated, are usually about 12-22. The frequency range of the cochlear implant is about 250 Hz to 8 kHz. Therefore, according to embodiments of the cochlear implant coding, about 12-22 units are selected from the neural code library in accordance with the electrode contacts of the cochlear implant for stimulation.

Once the one more neural units of the patient are selected, their pulse patterns are played to the cochlear implant patient via their CI. At step 140, the selected neural units of the patient are stimulated for sensing the acoustic pattern based on the selected neural response patterns. In one embodiment, the selected neural units of the patient are stimulated with electrical pulses that are coincident with the train of action potentials generated in the neural unit of the normal hearing animal in response to the receipt of the acoustic pattern.

In addition, the method may comprises optimizing the selection of the units for stimulation optimization based on feedback from the patient.

Further, the foregoing steps 110-140 are repeated consecutively for each acoustic pattern of the acoustic signal.

Figure 2:
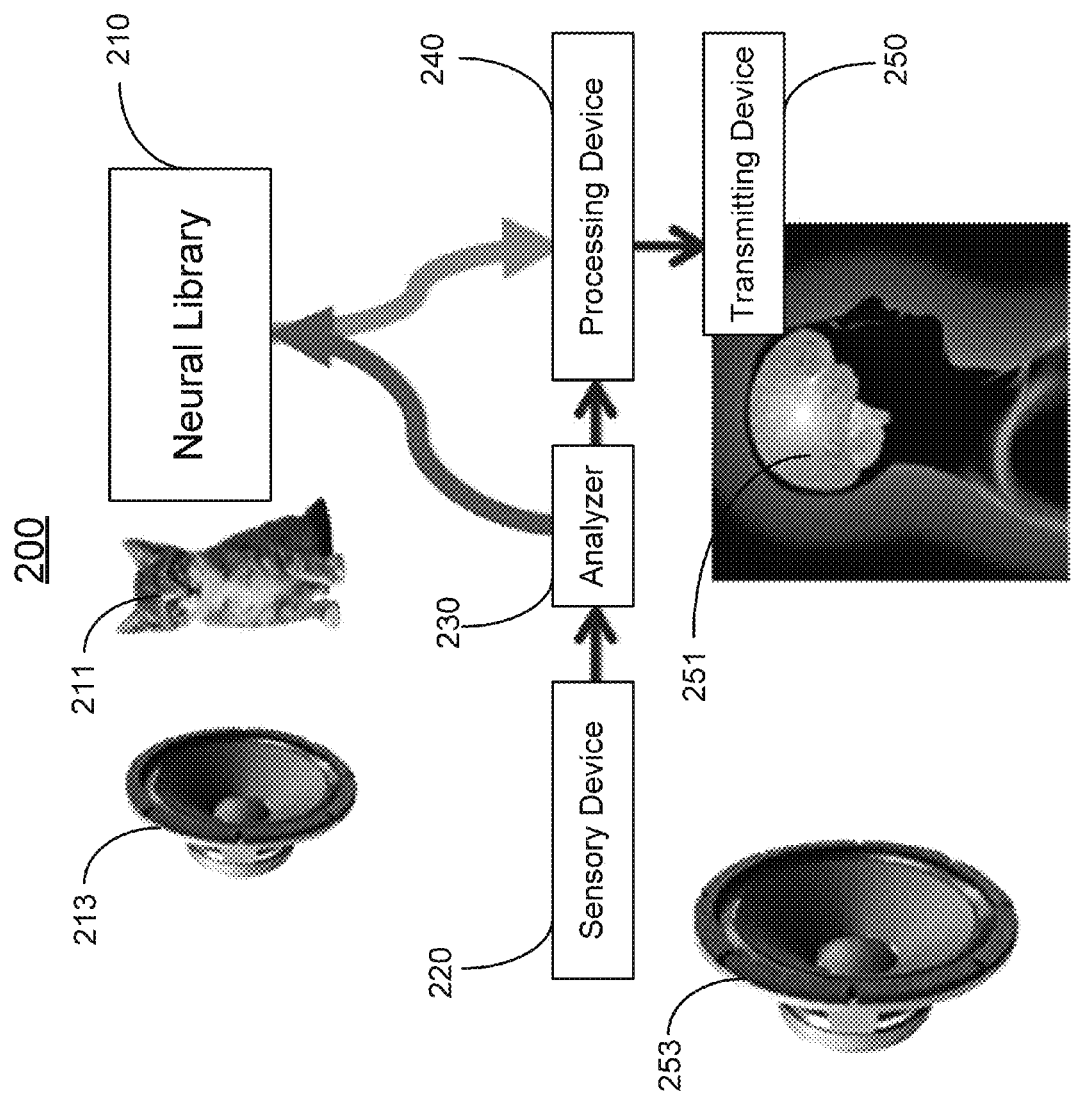
FIG. 2 shows schematically a system for cochlear implant coding for stimulation of a patient according to one embodiment of the invention.

Referring to FIG. 2, a system 200 for cochlear implant coding for stimulation of a patient is schematically shown according to one embodiment of the invention. In the embodiment, the system 200 has a neural code library 210, a sensory device 220, an analyzer 230, a processing device 240, and a transmitting device 250.

The neural code library 210 comprises a plurality of digital representations of neural responses of neural units of at least one normal hearing animal. In one embodiment, the normal hearing animal 211, e.g., a cat, is used to create the library for stimulation. Phonemes, syllables, and words are played via a speaker 213 to the animal 211 and the corresponding neural responses are recorded either from the auditory nerve, the cochlear nucleus or the inferior colliculus using multichannel electrodes. Likewise, repeated recordings can be made with single channel electrodes. Hereby, the location of the electrode determines the best frequency. For each of the phonemes, syllables or words, responses are recorded and stored in a library that is associated with the acoustic signal.

The sensory device 220 is configured to detect an acoustic signal, for example, played from a speaker 253. In one embodiment, the sensory device 220 comprises one or more microphones.

The analyzer 230 is in communication with the sensory device 220 and the neural library 210 via a wired or cable connection, or a wireless connection, and is configured to identify each acoustic pattern of the acoustic signal.

The processing device 240 is in communication with the neural code library 210 and the analyzer 230 via a wired or cable connection, or a wireless connection. The processing device 240 is configured, for each identified acoustic pattern, to retrieve a set of neural response patterns (digital representations of neural responses) corresponding to the identified acoustic pattern from the neural code library. Each neural response pattern contains a sequence of neural responses of a corresponding neural unit at its corresponding best frequency to the identified acoustic pattern. The processing device 240 is also configured, for each identified acoustic pattern, to select one or more neural units of the patient to be stimulated corresponding to electrode contacts (locations of the neural units) of a cochlear implant implanted in the patient and their neural response patterns from the retrieved set of neural response patterns.

The acoustic signal is recorded and the acoustic pattern is determined. Pattern is matched with acoustic pattern in the library. Since each identified acoustic pattern is linked to a series of neural patterns that were recorded from the animal, the recorded neural response can be used to stimulate the auditory nerve of the severe-to-profound deaf subject via the cochlear implant. Hereby, the optimal use of the sequences stored for the acoustic pattern is dynamic and is determined for each user with the help of a self-learning stochastic model, such as a Hidden Markov Model.

The transmitting device 250 is in communication with the processing device 240 and the cochlear implant 251 via a wired or cable connection, or a wireless connection. The transmitting device 250 is configured, for each identified acoustic pattern, to transmit the digital representations of neural responses corresponding to the selected neural response patterns to the electrodes of the cochlear implant as so to stimulate the selected neural units of the patient for sensing the acoustic signal.

According to the invention, to convert the acoustic signal into stimulation patterns of the cochlear implant, the system 200 continuously records the acoustic information and converts the acoustic signal into a track of voltage values obtained from the microphone. Overlapping frames are acquired. Hereby, each frame is continuously shifted every 10 ms or optimized otherwise. A Fast Fourier Transform of the signal provides the signal in the frequency domain and allows comparing the pattern of the speech signal with patterns stored in a library. Once a match is made with a phoneme, syllable, or word, the system outputs the corresponding stimulation pattern stored in the library for this word at the cochlear implant electrode. The stimulation pattern includes as many electrodes contacts along the cochlear implant array as possible. The stimulation library, which is obtained from neural recordings in a normal hearing animal, contains the neural responses from more than 100 possible frequencies for each word. Starting with a given initial distribution for stimulation channels, a stochastic model, such as a Hidden Markov Model, will select the optimal stimulation pattern for each word for the patient. The system is individualized for each patient and provides the best stimulation pattern for each individual and each word/syllable.

Figure 10:
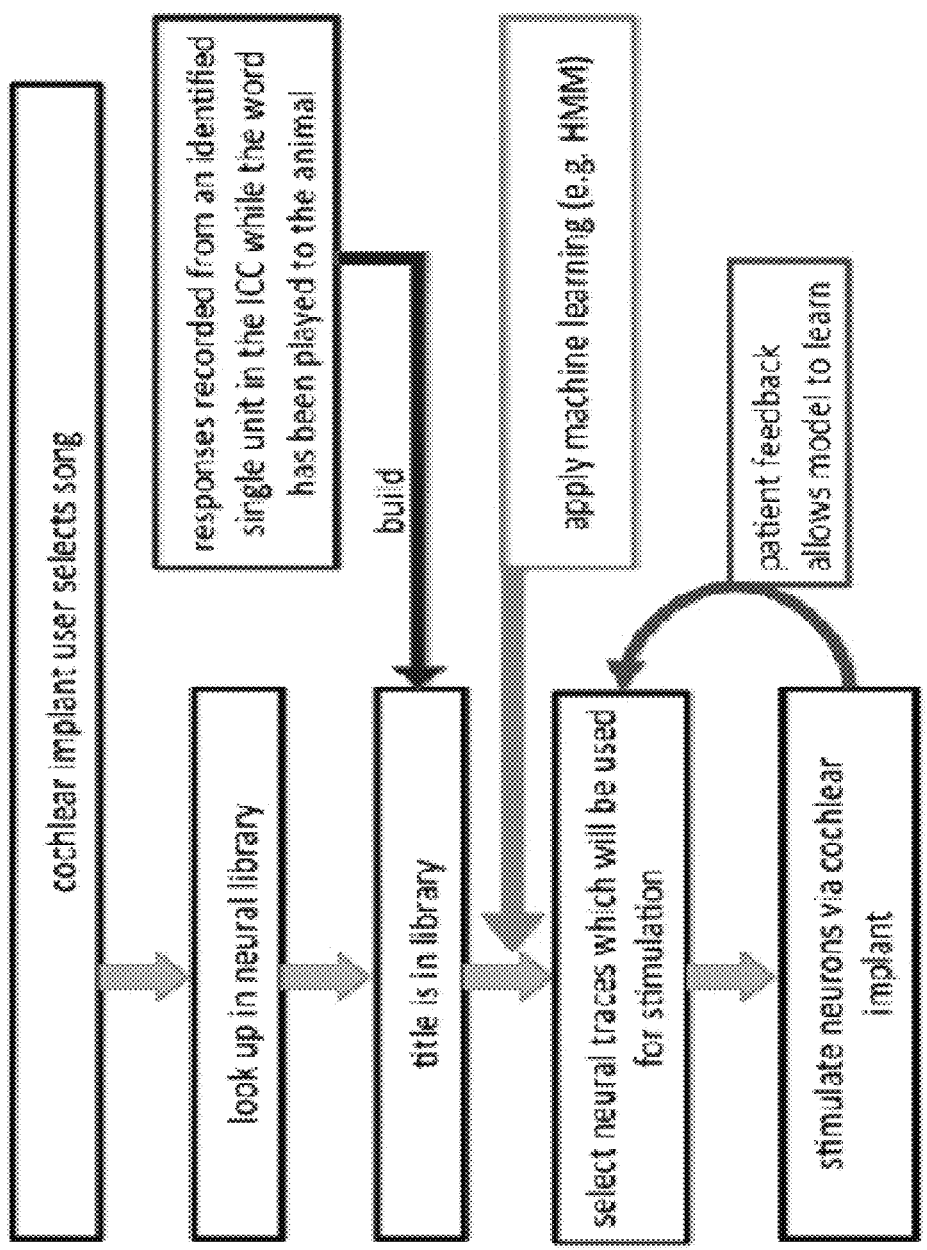
FIG. 10 shows schematically a flowchart for playing an acoustical signal to a patient having a cochlear implant implanted according to one embodiment of the invention.

FIG. 10 shows schematically a flowchart for playing an acoustic signal to a patient having a cochlear implant implanted according to one embodiment of the invention. In this exemplary embodiment, the neural code library or trans-species library may contain the neural response patterns of acoustic signals, i.e., the digital representations of neural responses of neural units corresponding to the acoustic signal, such as songs, speech, movies, stories, and so on, in additional to the neural response patterns of acoustic patterns such as phoneme, syllable, or word. The neural code library or trans-species library may be stored in local computers, servers, or cloud dives on the internet.

For predetermined music tunes—the tune box. At first, the cochlear implant user (patient) selects an acoustic signal such a song to be played. Then, the neural code library is looked up. The neural code library comprises neural responses of neural units of at least one normal hearing animal to a plurality of acoustic signals. In one embodiment, the neural responses of each neural unit of the normal hearing animal are acquired from neural recordings in the corresponding neural unit when each acoustic signal at the plurality of frequencies is played to the normal hearing animal. The neural responses of each neural unit of the normal hearing animal to each acoustic signal comprise neural response patterns. Each neural response pattern comprises a train of action potentials generated in a corresponding neural unit of the normal hearing animal responsive to the acoustic signal.

If the selected acoustic signal exists in the neural code library, neural units to be stimulated are selected according to electrode contacts of the cochlear implant implanted in the patient and the corresponding neural response patterns from the neural code library. Since for each acoustic signal, several neural responses exist in the neural code library, ordered by the tonotopic site along the cochlea in which they were recorded, an HHM is used to optimize the distribution of the patterns along the different contacts of the electrode array.

Next, the selected neural units of the patient are stimulated for listening to the acoustic signal, by applying electrical pulses that are coincident with the trains of action potentials generated in the corresponding neural units of the normal hearing animal in response to the receipt of the acoustic signal.

In certain embodiments, the method further comprises optimizing the selection of the units for stimulation optimization based on feedback from the patient.

In one aspect, the invention also relates to a system for playing an acoustic signal to a patient having a cochlear implant implanted. The system includes the neural code library comprising a plurality of digital representations of neural responses of neural units of at least one normal hearing animal to a plurality of acoustic signals, a processing device configured to look up the neural code library, and if the selected acoustic signal exists in the neural code library, select neural units of the patient to be stimulated corresponding to electrode contacts of the cochlear implant implanted in the patient and the corresponding neural response patterns (digital representations) from the neural code library, and a transmitting device configured to transmit electrical that are coincident with the trains of action potentials generated in the corresponding neural units of the normal hearing animal in response to the receipt of the acoustical signal to the electrodes of the cochlear implant to stimulate the selected units of the patient for listening to the acoustic signal.

In certain embodiments, the processing device is in communication with the neural code library via a wired or cable connection, or a wireless connection. The transmitting device is in communication with the processing device and the cochlear implant via a wired or cable connection, or a wireless connection. The transmitting device can be a wireless transmitting device, such as a Bluetooth wireless transmitter.

Accordingly, the novel coding strategy, among other things, decreases the power consumption of the cochlear implant, decreases the current spread during stimulation, and provides more stochastic stimulation pattern since stimulation is only done at threshold level. The stimulation along the cochlea has a more natural pattern since stimulus frequency and site are determined and optimized by the patient.

Reduction in power consumption: In the normal hearing listener, loudness is encoded by the increase in rate of action potentials on the auditory nerve and by the recruitment of auditory neurons. Recruitment describes the number of neurons that produce a response to the acoustic stimulation, which is increasing with increasing sound level. In contemporary devices, loudness is mostly encoded by an increase in current amplitude, which results in an increase of the average rate of action potentials on the auditory nerve. The dynamic range over which neurons increase their rate of action potentials is typically 6-12 dB. This is different to the dynamic-range for normal hearing listeners of about 120 dB. With the novel coding strategy, the stimulation current remains constant at threshold level and the increase in rate is achieved by an increase in number of pulses delivered by the cochlear implant system. Typically, the average number of action potentials delivered on a selected electrode contact is below 100 Hz. This is well below the typical average repetition rate of contemporary devices, which is more than 250 pulses per second.

With the novel coding strategy, the current level is at threshold all the time. This reduces the power consumption as a result of increasing the current level with increasing sound levels. The recruitment is achieved by adding more channels for stimulation.

Increase in stochastic firing and increase in selective stimulation: Another advantage of stimulating the neurons at threshold levels is the more stochastic firing of the neurons. Not every neuron is equal in size and excitability. Differences in the electrical properties of the cells are apparent at repetition rates for stimulation that times between successive pulses are shorter than the refractory period of the neurons, which is about 0.6 ms.

Moreover, at threshold current levels, only a spatially small population of neurons is activated. Stimulation is more selective and more independent channels for stimulation are feasible. Since the current level for stimulation is not changing over time, the average number neurons stimulated by the current from one electrode contact remains stable.

These and other aspects of the invention are further described in the following section. Without intend to limit the scope of the invention, further exemplary implementations of the same according to the embodiments of the invention are given below.

Preliminary experiments were conducted according to embodiments of the invention. 53 words from the commercially available Speech-In-Noise (SIN) test were played to the ear of an anesthetized guinea pig, while neural activity of an identified and stable single unit in the central nucleus of the inferior colliculus was recorded. The best frequency of the unit to pure tone acoustic stimulation was determined as well. After the conclusion of the experiments, spectrograms of the acoustic signal were produced, as shown in FIGS. 4-7. It can be seen that for the words "bean", "bomb", "shirt" and "tough", which are shown in the examples, the acoustic information is represented over the frequency range between 0.1 and 7 kHz. The black dots in FIGS. 4-7 show the corresponding neural responses, which were recorded from the guinea pig inferior colliculus. Each dot represents an action potential and each line of dots (train of action potentials) is a different unit. The location of the line along the y-axis is determined by the unit's best frequency to the pure tone stimulation. The trains of action potentials are converted into trains of electrical pulses, where the timing of the electrical pulses are the same as the occurrence of the action potentials. Because of the memory limitations of the computer to the cochlear implant interface, the Bionic Ear Data Collection System (BEDCS), only up to 10 of those trains of electrical pulses were selected and were played to cochlear implant users who participated in the study. All electrode contacts were used to simultaneously stimulate starting from the tip of the array. The basal 6 electrodes were left "empty" (no stimulation occurred via those electrodes). In this test, the natural frequency map of the CI user could not be reproduced because of the lack of the animal data. What is presented is a distorted selection of frequencies, missing frequency information above and below 1.9 kHz. Equal speech intelligibility was found for speech, which was either high-pass or low-pass filtered at about 1.9 kHz (French NR, Steinberg JC. 1947; Fletcher HM, Steinberg JC. 1929). During the test sessions, the subjects were asked to describe the lexical content and the hearing experience to the words. When the words were played with the initial selection of frequencies to the listener, they could identify different tracks. Although lexical information was wrong, the information was robust. For example, subject 2 (S2) could clearly identify replayed words in the sequences, which were presented in a random order. S2 volunteered the information that the speaker is a male (which is correct), even though S2 was not asked for this information.

Furthermore, the test subjects could identify rhythm and loudness changes of the sequence despite the current amplitude for stimulation was not changed. Parallel stimulation at neighboring electrodes was possible. Subject 1 (S1) described the words as drops falling into water, or a boat cruising through the water. For some words S1 described pitch changes and two beats. Seven other test subjects were exposed to the same stimulation paradigm. Because of the distortion of the frequency map we simplified the test an asked the test subject to perform a four-word forced-choice test: 21 recorded tracks were played to the test subject and after each track they were asked to select the correct word, as shown in FIG. 9. In about 32% they selected the correct word, as shown in FIG. 9. If two independent presentations of the words were combined the number of correct choices (or correct twice) the percentage was 17%. Interestingly, for the wrong associations, 38% of the same words were selected wrong twice. Even more interestingly, some words were selected by almost all test subjects, as shown in FIG. 9. In a detailed analysis of the experiments we realized that important acoustic information below 1 kHz and above 2 kHz was not presented to the CI user. To determine how such a distorted acoustic signal sounds when played to a normal hearing subject, we limited the acoustic content of the words to the frequency range, which was available to the CI users during testing. Low frequency information was largely missing. The words were unintelligible, but obviously contained lexical content, and the acoustic contend matched very well the hearing experience described by the two CI users. Encouraged by our initial results, we will optimize the experimental parameters for a larger series of CI users to be tested. The improvement includes the recording of spike sequences obtained from the inferior colliculus of a more suitable test animal. Chinchilla will be used, which have a hearing range from 0.02 to 16 kHz, similar to that of humans. While words and sentences of the SIN-test are played to the ear neural activity will be recorded from the ICC. Neural activity from more units in the correct frequency range can be selected. Selection will be done according to the spectrograms of the speech signals. By better matching the best frequency of the neurons content with the spectrograms one expects that the CI user is able to understand single words.

In brief, the invention, among other things, discloses the novel coding strategy, where excitation patterns to be used were recorded from the auditory nerve of a normal functioning cochlea and are stored in a neural code library. Matching an acoustic fingerprint directly with an excitation pattern along the cochlear implant electrode increases the number of independent channels for information transfer, and lead to stochastic firing of the nerve fibers and a significant decrease in power required by the device. Since the increase in pulse rate is not evoked by the increase in current level but by the timing the pulses are presented by the generator the current level can always be held at threshold level, and decrease the power consumption of the cochlear implant.

The foregoing description of the exemplary embodiments of the invention has been presented only for the purposes of illustration and description and is not intended to be exhaustive or to limit the invention to the precise forms disclosed. Many modifications and variations are possible in light of the above teaching.

For example, while the description above is primarily directed to systems and methods related to coding strategies for use with cochlear implants, it is understood that the solutions provided herein are well-suited for use across a wide range of neuromodulation devices.

As one example, a method for neuromodulation device coding may be used in connection with a variety of stimulations of a patient. In such an example, the method may be implemented according to the following steps:

identifying a pattern of a sensory signal;

retrieving one or more digital representations of a neural response corresponding to the identified pattern from a neural code library, wherein the neural code library comprises a plurality of digital representations of neural responses of neural units corresponding to each pattern;

selecting one or more neural units of a patient to be stimulated by a neuromodulation device associated with the patient based on the retrieved one or more digital representations of a neural response pattern; and stimulating the selected neural units of the patient.

In an application of haptic stimulation, the neuromodulation device coding method can be used to stimulate the perception and manipulation of human subjects using a neural code library that comprises a plurality of digital representations of neural responses of neural units of animals or humans in response to the receipt of touching signals.

As another example, the following method for neuromodulation device coding for stimulation of an epilepsy patient may be used in connection with a closed loop deep brain stimulator. In such an example, the method may be implemented according to the following steps:

identifying a pattern of pathological neural activity that heralds the beginning of epileptic activity;

retrieving one or more digital representations of a neural response corresponding to a therapeutic neural response for the identified pathological neural activity from a neural code library, wherein the neural code library comprises a digital representation of appropriate therapeutic neural responses that correspond to a library recorded from an animal, or a library algorithmically reconstructed to mimic the library based on the library recorded from an animal;

selecting one or more neural units of a patient to be stimulated by the deep brain stimulator associated with the patient based on the retrieved one or more digital representations of a neural response pattern; and using the deep brain stimulator to stimulate the selected neural units of the patient.

As yet another example, the following method for neuromodulation device coding for stimulation of a patient may be used in connection with a deep brain stimulator. In such an example, the method may be implemented according to the following steps:

either the patient or the neuromodulation device selects a desired neural signal from a neural code library;

retrieving one or more digital representations of a neural response corresponding to the identified pattern from a neural code library, wherein the neural code library comprises a digital representations of a neural response of neural units corresponding to each pattern;

selecting one or more neural units of a patient to be stimulated by the deep brain stimulator associated with the patient based on the retrieved one or more digital representations of a neural response pattern; and using the deep brain stimulator to stimulate the selected neural units of the patient.

As a further example, the following method for neuromodulation device coding for stimulation of a patient may be used in connection with a spinal cord stimulator. In such an example, the method may be implemented according to the following steps:

either the patient or the neuromodulation device selects a desired neural signal from a neural code library;

retrieving one or more digital representations of a neural response corresponding to the identified pattern from a neural code library, wherein the neural code library comprises a digital representations of a neural response of neural units corresponding to each pattern;

selecting one or more neural units of a patient to be stimulated by the deep brain stimulator associated with the patient based on the retrieved one or more digital representations of a neural response pattern; and using the spinal cord stimulator to stimulate the selected neural units of the patient.

As yet a further example, the following method for neuromodulation device coding for stimulation of a patient may be used in connection with a retinal implant. In such an example, the method may be implemented according to the following steps:

a visual signal is analyzed by a computer vision algorithm which is used to identify and select items from a scene based upon the patient's preselected scene complexity parameters;

the algorithm retrieves one or more digital representations of the scene items corresponding to the identified pattern from a neural code library, wherein the neural code library comprises digital representations of neural response of neural units corresponding to each pattern;

selecting one or more neural units of a patient to be stimulated by the retinal implant associated with the patient based on the retrieved one or more digital representations of a neural response pattern; and using the retinal implant to stimulate the selected neural units of the patient.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the invention pertains without departing from its spirit and scope. Accordingly, the scope of the invention is defined by the appended claims rather than the foregoing description and the exemplary embodiments described therein.

LIST OF REFERENCES

Clark, G. 1995. Cochlear implants: it's time to rethink. Am J Otol 16, 120-1; author reply 122-3.

Clark, G. 2003. Cochlear Implants: Fundamentals and Applications Springer, New York.

Dallos, P. 1973. The auditory periphery: Biophysics and physiology. In: Dallos, P., (Ed.), The auditory periphery: Biophysics and physiology. Academic Press, New York.

Dallos, P. 1992. The active cochlea. J Neurosci 12, 4575-85.

Dallos, P. 2003. Organ of Corti kinematics. J Assoc Res Otolaryngol 4, 416-21.

Davis, H. 1983. An active process in cochlear mechanics. Hear Res 9, 79-90.

Davis, R. O. 1986. The Personal Acoustics Lab (PAL): a microcomputer-based system for digital signal acquisition, analysis, and synthesis. Comput Methods Programs Biomed 23, 199-210.

Dudley, H. 1939. The Automatic Synthesis of Speech. Proceedings of the National Academy of Sciences of the United States of America 25, 377-83.

Durand, L. G., Pibarot, P. 1995. Digital signal processing of the phonocardiogram: review of the most recent advancements. Crit Rev Biomed Eng 23, 163-219.

Edgerton, B. J., Brimacombe, J. A. 1984. Effects of signal processing by the House-3M cochlear implant on consonant perception. Acta Otolaryngol Suppl 411, 115-23.

Edwards, E., Chang, E. F. 2013. Syllabic (approximately 2-5 Hz) and fluctuation (approximately 1-10 Hz) ranges in speech and auditory processing. Hearing research 305, 113-34.

Erickson, M. L., D'Alfonso, A. E. 2002. A comparison of two methods of formant frequency estimation for high-pitched voices. J Voice 16, 147-71.

Fishman, K. E., Shannon, R. V., and Slattery, W. H. 1997. Speech recognition as a function of the number of electrodes used in the SPEAK cochlear implant speech processor. Journal of Speech, Language and Hearing Research, 1201-1215.

Flint, P. W., Haughey, B. H., Lund, V. J., Niparko, J. K., Richardson, M. A., Robbins, K. T., & Thomas, J. R. 2010.

Cummings Otolaryngology—Head and Neck Surgery Mosby Elsevier, Philadelphia Pa.

Garnham, C., O'Driscoll, M., Ramsden, Saeed, S. 2002. Speech understanding in noise with a Med-El COMBI 40+ cochlear implant using reduced channel sets. Ear and hearing 23, 540-52.

Gaubitch, N. D., Ward, D. B., Naylor, P. A. 2006. Statistical analysis of the autoregressive modeling of reverberant speech. The Journal of the Acoustical Society of America 120, 4031-9.

Hochmair, E. S., Hochmair-Desoyer, I. J., Burian, K. 1979. Experience with implanted auditory nerve stimulator. Trans Am Soc Artif Intern Organs 25, 357-61.

Hudspeth, A. J. 1989 Oct 5. How the ear's works work. Nature 341, 397-404.

Kiefer, J., von Ilberg, C., Rupprecht, V., Hubner-Egner, J., Knecht, R. 2000. Optimized speech understanding with the continuous interleaved sampling speech coding strategy in patients with cochlear implants: effect of variations in stimulation rate and number of channels. The Annals of otology, rhinology, and laryngology 109, 1009-20.

Kob, M., Neuschaefer-Rube, C. 2002. A method for measurement of the vocal tract impedance at the mouth. Med Eng Phys 24, 467-71.

Prather, J. F. 2013. Auditory signal processing in communication: perception and performance of vocal sounds. Hearing research 305, 144-55.

Rubinstein, J. T. 2004. How cochlear implants encode speech. Current opinion in otolaryngology and head and neck surgery 12, 444-448.

Scott, S. K., McGettigan, C. 2013. The neural processing of masked speech. Hearing research 303, 58-66.

Somek, B., Fajt S., Dembitz, A., Ivkovic, M., & Ostojic, J. 2006. Coding Strategies for Cochlear Implants AUTOMATIKA: casopis za automatiku, mjerenje, elektroniku, racunarstvo I komunikasije 47.

Stephens, J.D., Holt, L.L. 2011. A standard set of American-English voiced stop-consonant stimuli from morphed natural speech. Speech Commun 53, 877-888.

von Békésy, G. 1960. Experiments in Hearing McGraw-Hill Book Company, New York.

Wang, S., Mannell, R., Newall, P., Han, D. 2011. Contribution of spectral cues to mandarin lexical tone recognition in normal-hearing and hearing-impaired Mandarin Chinese speakers. Ear Hear 32, 97-103.

Wang, X. 2013. The harmonic organization of auditory cortex. Front Syst Neurosci 7, 114.

Wilson, B.S. 1997. The future of cochlear implants. British journal of audiology 31, 205-25.

Wilson, B. S., Dorman, M. F. 2008. Cochlear implants: a remarkable past and a brilliant future. Hearing research 242, 3-21.

French NR, Steinberg JC. 1947. Factors governing the intelligibility of speech sounds. JASA 19, 90-119.

Fletcher HM, Steinberg JC. 1929. Articulation testing methods. Bell Systems Tech J 8, 806-854.

Clark, G. M., Dowell, R. C., Pyman, B. C., Brown, A. M., Webb, R. L., Tong, Y. C., . . . Seligman, P. M. (1984). Clinical trial of a multi-channel cochlear prosthesis: results on 10 postlingually deaf patients. Aust N Z J Surg, 54(6), 519-526.

Clark, G. M., Tong, Y. C., Patrick, J. F., Seligman, P. M., Crosby, P. A., Kuzma, J. A., and Money, D. K. (1984). A multi-channel hearing prosthesis for profound-to-total hearing loss. J Med Eng Technol, 8(1), 3-8.

Djourno, A., and Eyries, C. (1957). [Auditory prosthesis by means of a distant electrical stimulation of the sensory nerve with the use of an indwelt coiling]. Presse Med, 65(63), 1417.

Doyle, J. B., Jr., Doyle, J. H., Turnbull, F. M., Abbey, J., and House, L. (1963). Electrical Stimulation in Eighth Nerve Deafness. A Preliminary Report. Bull Los Angel Neuro Soc, 28, 148-150.

House, W. F., and Berliner, K. I. (1982). The cochlear implant. Otolaryngol Clin North Am, 15(4), 917-923.

House, W. F., and Edgerton, B. J. (1982). A multiple-electrode cochlear implant. Ann Otol Rhinol Laryngol Suppl, 91(2 Pt 3), 104-116.

Lawson, D. T., Wilson, B. S., & Finley, C. C. (1993). New processing strategies for multichannel cochlear prostheses. Prog Brain Res, 97, 313-321.

Shannon, R. V. (1981). Growth of loudness for sinusoidal and pulsatile electrical stimulation. Ann Otol Rhinol Laryngol Suppl, 90(2 Pt 3), 13-14.

Shannon, R. V. (1983). Multichannel electrical stimulation of the auditory nerve in man. II. Channel interaction. Hear Res, 12(1), 1-16.

Shannon, R. V. (1985). Threshold and loudness functions for pulsatile stimulation of cochlear implants. Hear Res, 18(2), 135-143.

Shannon, R. V., Fu, Q. J., and Galvin, J., 3rd. (2004). The number of spectral channels required for speech recognition depends on the difficulty of the listening situation. Acta Otolaryngol Suppl (552), 50-54.

Simmons, F. B., Dent, L. J., and Van Compernolle, D. (1986). Comparison of different speech processing strategies on patients receiving the same implant. Ann Otol Rhinol Laryngol, 95(1 Pt 1), 71-75.

Simmons, F. B., Mathews, R. G., Walker, M. G., and White, R. L. (1979). A functioning multichannel auditory nerve stimulator. A preliminary report on two human volunteers. Acta Otolaryngol, 87(3-4), 170-175.

Wilson, B. S. (1997). The future of cochlear implants. Br J Audiol, 31(4), 205-225.

Wilson, B. S., Finley, C. C., Lawson, D. T., Wolford, R. D., Eddington, D. K., and Rabinowitz, W. M. (1991). Better speech recognition with cochlear implants. Nature, 352 (6332), 236-238. doi: 10.1038/352236a0

Wilson, B. S., Finley, C. C., Lawson, D. T., Wolford, R. D., and Zerbi, M. (1993). Design and evaluation of a continuous interleaved sampling (CIS) processing strategy for multichannel cochlear implants. J Rehabil Res Dev, 30(1), 110-116.

What is claimed is:

1. A method for neuromodulation device coding for stimulation of a patient, comprising:
   (a) identifying, by an analyzer, a pattern of a sensory signal;
   (b) retrieving, by a processing device, one or more digital representations of a neural response corresponding to the identified pattern from a neural code library, wherein the neural code library comprises a plurality of digital representations of neural responses of neural units of at least one normal functioning animal, wherein each of the plurality of digital representations of neural responses corresponds to one of a plurality of digital representations of acoustic patterns;
   (c) selecting, by the processing device, one or more neural units of the patient to be stimulated by a neuromodulation device associated with the patient based on the retrieved one or more digital representations of a neural response pattern; and (d) stimulating, by a transmitting device in communication with the processing device and the neuromodulation device, the selected neural units of the patient.

2. The method of claim 1, wherein the neuromodulation device is implanted in the patient.

3. The method of claim 2, wherein the neuromodulation device is a cochlear implant.

4. The method of claim 1, wherein each neural unit is an identifiable and stable single unit in at least one of the inferior colliculus, cochlear nucleus, auditory nerve, cortex, brainstem, and midbrain of the normal functioning animal.

5. The method of claim 1, wherein the neural responses of neural units of the normal functioning animal are acquired from neural recordings in the neural units when each pattern is played to the normal functioning animal at a plurality of frequencies.

6. The method of claim 5, wherein each neural response pattern contains a sequence of neural responses of a corresponding neural unit at its corresponding best frequency to the identified pattern.

7. The method of claim 6, wherein the neural response of each neural unit of the normal functioning animal comprises a train of action potentials generated in the neural unit of the normal functioning animal in response to the receipt of the identified pattern.

8. The method of claim 7, wherein the selected neural units of the patient are simulated with electrical pulses that are coincident with the trains of action potentials generated in the corresponding neural units of the normal functioning animal in response to the receipt of the identified pattern.

9. The method of claim 1, wherein the pattern is a segment or a frame of the sensory signal.

10. The method of claim 9, wherein the sensory signal is an acoustic signal.

11. The method of claim 10, wherein the pattern comprises a phoneme, a syllable, a word, words, or a combination thereof.

12. The method of claim 1, further comprising repeating steps (a)-(d) consecutively for each pattern of the sensory signal.

13. The method of claim 10, wherein the step of identifying the pattern of the sensory signal is performed with a speech recognition algorithm.

14. The method of claim 1, wherein the step of retrieving one or more digital representations of a neural response corresponding to the identified pattern from the neural code library is performed with a stochastic model including a Hidden Markov Model (HMM).

15. The method of claim 1, further comprising optimizing the selection of the units for stimulation optimization based on feedback from the patient.

16. A system for cochlear implant coding for stimulation of a patient, comprising:
(a) a neural code library comprising a plurality of digital representations of neural responses of neural units of at least one normal hearing animal, wherein each of the plurality of digital representations of neural responses corresponds to one of a plurality of digital representations of acoustic patterns;
(b) a sensory device configured to detect an acoustic signal;
(c) an analyzer in communication with the sensory device, configured to identify one of the digital representations of acoustic patterns in the neural code library in response to the receipt of the acoustic signal;
(d) a processing device in communication with the neural code library and the analyzer, configured, for each identified acoustic pattern, to
retrieve the digital representations of neural responses of neural units corresponding to the identified acoustic pattern from the neural code library; and
select one or more neural units of the patient to be stimulated by a cochlear implant implanted in the patient; and
(e) a transmitting device in communication with the processing device and the cochlear implant, configured to stimulate the selected one or more neural units of the patient.

17. The system of claim 16, wherein the digital representations of the neural responses include data for each of a plurality of frequencies.

18. The system of claim 17, wherein each neural response pattern contains a sequence of neural responses of a corresponding neural unit at its corresponding best frequency to the identified acoustic pattern.

19. The system of claim 18, wherein the best frequency of a neural unit is a frequency for pure tone stimulation that needs a lowest sound level to evoke a neural response in the corresponding unit.

20. The system of claim 16, wherein each neural unit is an identifiable and stable single unit in at least one of the inferior colliculus, cochlear nucleus, auditory nerve, brainstem, and midbrain of the normal hearing animal.

21. The system of claim 16, wherein the neural responses of neural units of the normal hearing animal are acquired from neural recordings in the neural units when each acoustical pattern is played to the normal hearing animal at a plurality of frequencies.

22. The system of claim 21, wherein the neural response of each neural unit of the normal hearing animal comprises a train of action potentials generated in the neural unit of the normal hearing animal in response to the receipt of the acoustical pattern.

23. The system of claim 22, wherein the selected one or more neural units of the patient are stimulated with electrical pulses that are coincident with the trains of action potentials generated in the corresponding neural units of the normal hearing animal in response to the receipt of the acoustical pattern.

24. The system of claim 16, wherein the acoustical pattern is a segment or a frame of the acoustical signal.

25. The system of claim 24, wherein the acoustical pattern comprises a phoneme, a syllable, a word, words, or a combination thereof.

26. The system of claim 16, wherein the sensory device comprises one or more microphones.

27. The system of claim 16, wherein the electrodes of the cochlear implant comprise an electrode array with multiple electrode contacts.

28. The system of claim 16, wherein the processing device is in communication with the neural code library and the analyzer via a wired or cable connection, or a wireless connection.

29. The system of claim 16, wherein the transmitting device is in communication with the processing device and the cochlear implant via a wired or cable connection, or a wireless connection.

30. The system of claim 29, wherein the transmitting device is a wireless transmitting device.

31. The system of claim 30, wherein the wireless transmitting device is a Bluetooth wireless transmitter.

32. A method for playing an acoustical signal to a patient having a cochlear implant implanted, comprising:
(a) selecting an acoustical signal which the patient wants to listen to;
(b) looking up, by a processing device, a neural code library, wherein the neural code library comprises a plurality of digital representations of neural responses of neural units of at least one normal hearing animal, wherein each of the plurality of digital representations of neural responses corresponds to one of a plurality of digital representations of acoustic signals and comprises a neural response pattern;
(c) when the selected acoustical signal exists in the neural code library, selecting, by the processing device, one or more neural units of the patient to be stimulated by the cochlear implant implanted in the patient; and
(d) stimulating, by a transmitting device in communication with the processing device and the cochlear implant, the selected one or more neural units of the patient for listening to the acoustical signal.

33. The method of claim 32, wherein each neural unit is an identifiable and stable single unit in at least one of the inferior colliculus, cochlear nucleus, auditory nerve, brainstem, and midbrain of the normal hearing animal.

34. The method of claim 32, wherein the neural responses of neural units of the normal hearing animal are acquired from neural recordings in the neural units when each acoustical signal is played to the normal hearing animal at a plurality of frequencies.

35. The method of claim 34, wherein each neural response pattern comprises a train of action potentials generated in a corresponding neural unit of the normal hearing animal in response to the receipt of the acoustical signal.

36. The method of claim 32, wherein the selected one or more neural units of the patient are stimulated with electrical pulses that are coincident with the trains of action potentials generated in the corresponding neural units of the normal hearing animal in response to the receipt of the acoustical signal.

37. The method of claim 36, further comprising optimizing the selection of the units for stimulation optimization based on feedback from the patient.

38. A system for playing an acoustic signal to a patient having a cochlear implant implanted comprising:
(a) a neural code library comprising a plurality of digital representations of neural responses of neural units of at least one normal hearing animal, wherein each of the plurality of digital representations of neural responses corresponds to one of a plurality of digital representations of acoustic patterns and comprises a neural response pattern;
(d) a processing device in communication with the neural code library, configured to look up the neural code library, and when the selected acoustical signal exists in the neural code library, select one or more neural units of the patient to be stimulated by the cochlear implant implanted in the patient; and
(e) a transmitting device in communication with the processing device and the cochlear implant, configured to stimulate the selected one or more neural units of the patient for listening to the acoustical signal.

39. The system of claim 38, wherein each neural unit is an identifiable and stable single unit in at least one of the inferior colliculus, cochlear nucleus, auditory nerve, brainstem, and midbrain of the normal hearing animal.

40. The system of claim 39, wherein the neural responses of neural units of the normal hearing animal are acquired from neural recordings in the neural units when each acoustical pattern is played to the normal hearing animal at a plurality of frequencies.

41. The system of claim 40, wherein each neural response pattern comprises a train of action potentials generated in a corresponding neural unit of the normal hearing animal in response to the receipt of the acoustical signal.

42. The system of claim 41, wherein the selected one or more neural units of the patient are stimulated with electrical pulses that are coincident with the train of action potentials generated in the neural unit of the normal hearing animal in response to the receipt of the acoustical signal.

43. The system of claim 38, wherein electrodes of the cochlear implant comprise an electrode array with multiple electrode contacts.

44. The system of claim 38, wherein the processing device is in communication with the neural code library via a wired or cable connection, or a wireless connection.

45. The system of claim 38, wherein the transmitting device is in communication with the processing device and the cochlear implant via a wired or cable connection, or a wireless connection.

46. The system of claim 45, wherein the transmitting device is a wireless transmitting device.

47. The system of claim 46, wherein the wireless transmitting device is a Bluetooth wireless transmitter.

* * * * *